US012776300B2

(12) United States Patent
Murai Von Bünau

(10) Patent No.: US 12,776,300 B2
(45) Date of Patent: Oct. 27, 2026

(54) VOICE GRAFTING USING MACHINE LEARNING

(71) Applicant: Altavo GmbH, Dresden (DE)

(72) Inventor: Rudolf Murai Von Bünau, Jena (DE)

(73) Assignee: Altavo GmbH, Dresden (DE)

(*) Notice: Subject to any disclaimer, the term of this patent is extended or adjusted under 35 U.S.C. 154(b) by 358 days.

(21) Appl. No.: 17/916,879

(22) PCT Filed: Apr. 20, 2021

(86) PCT No.: PCT/EP2021/060251

§ 371 (c)(1),
(2) Date: Oct. 4, 2022

(87) PCT Pub. No.: WO2021/214065

PCT Pub. Date: Oct. 28, 2021

(65) Prior Publication Data

US 2023/0154450 A1 May 18, 2023

(30) Foreign Application Priority Data

Apr. 22, 2020 (DE) ........................ 102020110901.6

(51) Int. Cl.
*G10L 13/033* (2013.01)
*A61F 2/20* (2006.01)
(Continued)

(52) U.S. Cl.
CPC .............. *G10L 13/033* (2013.01); *A61F 2/20* (2013.01); *G10L 15/25* (2013.01); *G10L 21/00* (2013.01);
(Continued)

(58) Field of Classification Search
CPC ....... G10L 13/033; G10L 15/25; G10L 21/00; G10L 25/30; G10L 2021/0135; A61F 2/20; A61F 2002/206; A61F 2250/0002
See application file for complete search history.

(56) References Cited

U.S. PATENT DOCUMENTS 5,729,694 A 3/1998 Holzrichter
6,006,175 A 12/1999 Holzrichter
(Continued)

FOREIGN PATENT DOCUMENTS

DE 202004010342 U1 11/2004
DE 10 2009 023 924 A1 12/2010
EP 2577552 B1 4/2013

OTHER PUBLICATIONS

Gilbert, James, Jose Gonzalez, Lam Cheah, Stephen Ell, Phil Green, Roger Moore, and Ed Holdsworth, "Restoring speech following total removal of the larynx by a learned transformation from sensor data to acoustics", 2017, 2017 Acoustical Society of America Journal, vol. 141, No. 3, pp. EL307-EL313. (Year: 2017).*
(Continued)

*Primary Examiner* — James Boggs
(74) *Attorney, Agent, or Firm* — Tucker Ellis LLP

(57) ABSTRACT

A process labeled "voice grafting" can be understood in terms of the source-filter model of speech production as follows: For a patient who has partially or completely lost the ability to phonate, but retained at least a partial ability to articulate, the techniques described herein computationally "graft" the patient's time varying filter function, i.e. articulation, onto a source function, i.e. phonation, which is based on the speech output of one or more healthy speakers, in order to synthesize natural sounding speech in real time.

12 Claims, 6 Drawing Sheets

(51) Int. Cl.

| | |
|---|---|
| ***G10L 15/25*** | (2013.01) |
| ***G10L 21/00*** | (2013.01) |
| ***G10L 25/30*** | (2013.01) |
| *G10L 21/013* | (2013.01) |

(52) U.S. Cl.

CPC ........ *G10L 25/30* (2013.01); *A61F 2002/206* (2013.01); *A61F 2250/0002* (2013.01); *G10L 2021/0135* (2013.01)

(56) References Cited

U.S. PATENT DOCUMENTS

| | | | | |
|---|---|---|---|---|
| 7,162,415 | B2 | 1/2007 | Holzrichter | |
| 7,191,105 | B2 | 3/2007 | Holzrichter | |
| 10,283,120 | B2* | 5/2019 | Gilbert | G10L 13/04 |
| 10,878,818 | B2* | 12/2020 | Kapur | A61B 5/6814 |
| 11,361,783 | B2* | 6/2022 | Tsai | G06F 3/167 |
| 2012/0053931 | A1 | 3/2012 | Holzrichter | |
| 2012/0136660 | A1* | 5/2012 | Harman | G10L 15/24 704/E15.005 |
| 2013/0332173 | A1 | 12/2013 | Callahan | |
| 2017/0263237 | A1* | 9/2017 | Green | G10L 13/04 |
| 2018/0358003 | A1 | 12/2018 | Calle et al. | |
| 2020/0126557 | A1* | 4/2020 | Lee | G10L 15/22 |
| 2022/0208173 | A1* | 6/2022 | Chang | A61B 5/37 |

OTHER PUBLICATIONS

Kimura, Naoki, Michinari Kono, and Jun Rekimoto, "SottoVoce: An Ultrasound Imaging-Based Silent Speech Interaction Using Deep Neural Networks", May 2019, Proceedings of the 2019 CHI Conference on Human Factors in Computing Systems, pp. 1-11. (Year: 2019).*

Korzekwa, Daniel, Roberto Barra-Chicote, Bozena Kostek, Thomas Drugman, and Mateusz Lajszczak, "Interpretable Deep Learning Model for the Detection and Reconstruction of Dysarthric Speech", Sep. 2019, Interspeech 2019, pp. 3890-3894. (Year: 2019).*

Shin, Young Hoon, and Jiwon Seo, "Towards Contactless Silent Speech Recognition Based on Detection of Active and Visible Articulators Using IR-UWB Radar", Oct. 2016, Sensors, vol. 16, No. 11, pp. 1-19. (Year: 2016).*

Hueber, Thomas, Elie-Laurent Benaroya, Gérard Chollet, Bruce Denby, Gérard Dreyfus, and Maureen Stone, "Development of a silent speech interface driven by ultrasound and optical images of the tongue and lips", Nov. 2009, Speech Communication, vol. 52, No. 4, pp. 288-300. (Year: 2009).*

Taguchi, Fumiaki, and Tokihiko Kaburagi, "Articulatory-to-speech Conversion Using Bi-directional Long Short-term Memory", Sep. 2018, Interspeech 2018, pp. 2499-2503. (Year: 2018).*

Meltzner, Geoffrey, James Heaton, Yunbin Deng, Gianluca De Luca, Serge Roy, and Joshua Kline, "Silent Speech Recognition as an Alternative Communication Device for Persons with Laryngectomy", 2017, IEEE/ACM Transactions on Audio, Speech and Language Processing, vol. 25, No. 12, pp. 2386-2398. (Year: 2017).*

Gonzalez, Jose, Lam Cheah, James Gilbert, Jie Bai, Stephen Ell, Phil Green, and Roger Moore, "Voice Restoration after Laryngectomy based on Magnetic Sensing of Articulator Movement and Statistical Articulation-to-Speech Conversion", 2017, Communications in Computer and Information Science. (Year: 2017).*

Cai, Jun, Thomas Hueber, Sotiris Manitsaris, Pierre Roussel, Lise Crevier-Buchman, Maureen Stone, Claire Pilot-Loiseau, Gerard Chollet, Gerard Dreyfus, and Bruce Denby, "Vocal Tract Imaging System for Post-Laryngectomy Voice Replacement", May 2013, 2013 IEEE 12MTC, pp. 676-680. (Year: 2013).*

Birkholz, Peter, Simon Stone, Klaus Wolf, and Dirk Plettemeier, "Non-Invasive Silent Phoneme Recognition Using Microwave Signals", Dec. 2018, IEEE/ACM Transactions on Audio, Speech and Language Processing (TASLP), vol. 26, No. 12, pp. 2404-2411. (Year: 2018).*

Taguchi, Fumiaki, and Tokihiko Kaburagi, "Articulatory-to-speech conversion using bi-directional long short-term memory", Sep. 2018, Proceedings of the Annual Conference of the International Speech Communication Association (Interspeech 2018), pp. 2499-2503. (Year: 2018).*

Ma, Yue, Hong Hong, Hui Li, Heng Zhao, Yusheng Li, Li Sun, Chen Gu, and Xiaohua Zhu, "Non-Contact Speech Recovery Technology Using a 24 GHz Portable Auditory Radar and Webcam", Feb. 2020, Remote Sensing 2020, vol. 12, No. 653, pp. 1-16. (Year: 2020).*

Csapó, Tamás Gábor, Mohammed Salah Al-Radhi, Géza Németh, Gábor Gosztolya, Tamás Grosz, László Tóth, and Alexandra Markó, "Ultrasound-based Silent Speech Interface Built on a Continuous Vocoder", Sep. 2019, Interspeech 2019, pp. 894-898. (Year: 2019).*

Gonzalez, Jose, Lam Cheah, Angel Gomez, Phil Green, James Gilbert, Stephen Ell, Roger Moore, Ed Holdsworth, "Direct Speech Reconstruction from Articulatory Sensor Data by Machine Learning", Dec. 2017, IEEE/ACM Transactions on Audio, Speech and Language Processing, vol. 25, No. 12, pp. 2362-2374. (Year: 2017).*

Yue Ma, et al., "Non-Contact Speech Recovery Technology Using a 24 GHZ Portable Auditory Radar and Webcam", Remote Sensing, (2020), 16 pages.

International Search Report and Written Opinion from corresponding International Application No. PCT/EP2021/060251, mailed on Jul. 26, 2021, 10 pages.

Gilbert, James et al., "Restoring speech following total removal of the larynx by a learned transformation from sensor data to acoustics", The Journal of the Acoustical Society of America, American Institute of Physics for the Acoustical Society of America, vol. 141, No. 3, Mar. 21, 2017, 8 pages.

Kimura, Naoki et al., "SottoVoce: An Ultrasound Imaging-Based Silent Speech Interaction Using Deep Neural Networks", Human Factors in Computing Systems, CHI 2019 Paper 146, May 4-9, 2019, 12 pages.

Janke, Matthias et al., "EMG-to-Speech: Direct Generation of Speech From Facial Electromyographic Signals", IEEE/ACM Trasactions on Audio, Speech, and Language Processing, vol. 25, No. 12, Dec. 2017, 12 pages.

Gonzalez, Jose A. et al., "Direct Speech Reconstruction from Articulatory Sensor Data by Machine Learning", IEEE/ACM Transactions on Audio, Speech, and Language Processing, vol. 25, No. 12, Dec. 2017, 14 pages.

Denby. B. et al., "Silent Speech Interfaces", Speech Communication 52 (2010), 270-287, Aug. 20, 2009, 18 pages.

Peter Birkholz et al.: "Non-invasive silent phoneme recognition using microwave signals"; IEEE/ACM Transactions on Audio, Speech, and Language Processing; dated 2018; 8 pages.

Matthias Janke et al.: "EMG-to-Speech: Direct Generation of Speech from Facial Electromyohraphic Signals"; IEEE/ACM Transactions on Audio, Speech, and Language Processing; 10 pages.

Ian Vince McLoughlin: "The Use of Low-Frequency Ultrasound for Voice Activity Detection"; National Engineering Laboratory of Speech and Language Information Processing; dated 2014, 5 pages.

Ian Vince McLoughlin: "Low Frequency Ultrasonic Voice Activity Detection using Convolutional Neural Networks"; dated 2015; 5 pages.

Anne Holden: "Columbia Engineers Translate Brain Signals Directly into Speech"; Mortimer B. Zuckerman and Mind Brain Behavior Institute; 3 pages.

Hassan Akbari et al.: "Towards reconstructing intelligible speech from the human auditory cortex"; Scientific Reports; published Jan. 29, 2019; 12 pages.

David A. Moses et al.: "Real-time decoding of question-and-answer speech dialogue using human cortical activity"; Nature Communications; dated 2019; 14 pages.

Victor Passy et al.: "Tracheostomy Speaking Valve on Ventilator-Dependent Patients"; Laryngoscope; dated Jun. 1993; 1 page.

P. Kress et al.: "Are modern voice prostheses better? A lifetime comparison of 749 voice prostheses"; Eur Arch Otorhinolaryngol; dated 2014; 8 pages.

Rachel Kaye et al.: "The electrolarynx: voice restoration after total laryngectomy"; Medical Devices: Evidence and Research; dated Jun. 21, 2017; 8 pages.

(56) References Cited

OTHER PUBLICATIONS

Cara E. Stepp: "Surface electromyography for speech and swallowing systems: Measurement, analysis, and Interpretation"; JSLHR Papers in Press; published Jan. 9, 2012; 46 pages.
Gabrielle L. Hands et al.: "Effect of Age on Human-Computer Interface Control via Neck Electromyography"; Interact Comput; dated 2016; 8 pages.
Meredith J. Cler et al.: "Surface electromyographic control of a novel phonemic interface for speech synthesis"; Augmentative and Alternative Communication; dated 2016; 11 pages.
Geoffrey S. Meltzner et al.: "Speech Recognition for Vocalized and Subvocal Modes of Production using Surface EMG Signals from the Neck and Face"; dated 2008; 4 pages.
Bruce Denby et al.: "Speech Synthesis from real time ultrasound images of the tongue"; IEEE; dated 2004; 4 pages.
Bruce Denby et al.: "Prospects for a silent speech interface using ultrasound imaging"; IEEE, dated 2006; 4 pages.
T. Hueber et al.: "Eigentongue Feature Extraction for an Ultrasound-based Silent Speech Interface"; IEEE, dated 2007; 4 pages.
T. Hueber et al.: "Development of a Silent Speech Interface Driven by Ultrasound and Optical Images of the Tongue and Lips"; Speech Communication; dated 2009; 32 pages.
T. Hueber: "Speech Synthesis from ultrasound and optical images of the speaker's vocal tract"; 9 pages.
L.C. Ng et al.: "Low Bandwidth Vocoding Using EM Sensor and Acoustic Signal Processing"; dated 2001; 6 pages.
J.F. Holzrichter: "New Ideas for Speech Recognition and Related Technologies"; dated 2002; 69 pages.
J.F. Holzrichter: "Real-Time Speech Masking Using EM-Wave Acoustic Sensors"; 38th International Conference on Acoustics, Speech, and Signal Processing; dated 2012; 7 pages.
K. Mostov et al.: "Medical applications of shortwave FM radar: Remote monitoring of cardiac and respiratory motion"; Am. Assoc. Phys. Med.; dated 2010; 7 pages.
Mingke Jiao et al.: "A Novel Radar Sensor for the Non-Contact Detection of Speech Signals"; Sensors; dated 2010; 12 pages.
Sheng Li et al.: "A 94-GHz Millimeter-Wave Sensor for Speech Signal Acquisition"; Sensors; dated 2013; 13 pages.
Jaime Lien et al.: "Soli: Ubiquitous Gesture Sensing with Millimeter Wave Radar"; ACM Trans. Graph., vol. 35, No. 4, Article 142,; dated 2016; 19 pages.
Saiwen Wang et al.: "Interacting with Soli: Exploring Fine-Grained Dynamic Gesture Recognition in the Radio-Frequency Spectrum"; ETH Zurich, 2Google ATAP; dated 2016; 10 pages.
Reutter: "Prosthetic voice rehabilitation after total Laryngeal removal—a historical treatise since Billroth (1873)"; From the Section for Phoniatrics and Pediatric Audiology; dated 2007, 368 with translation.
Chung, Joon Son, et al., "Lip Reading in Profile", British Machine Vision Association and Society for Pattern Recognition, 2017, pp. 1-11.
Shillingford, Brendan, et al., "Large-Scale Visual Speech Recognition", Interspeech, 2019, pp. 1-21.
Makino, Takaki, et al., "Recurrent Neural Network Transducer for Audio-Visual Speech Recognition", IEEE Automatic Speech Recognition and Understanding Workshop, 2019, 8 pages.
Wand, Michael, et al., "Array-based Electromyographic Silent Speech Interface", Biosignals, 2013, pp. 89-96.
Cler, Meredith J., et al., "Surface electromyographic control of speech synthesis", 36th Annual International Conference of the IEEE Engineering in Medicine and Biology Society, 2014, pp. 5848-5851.

* cited by examiner

Fig. 7·
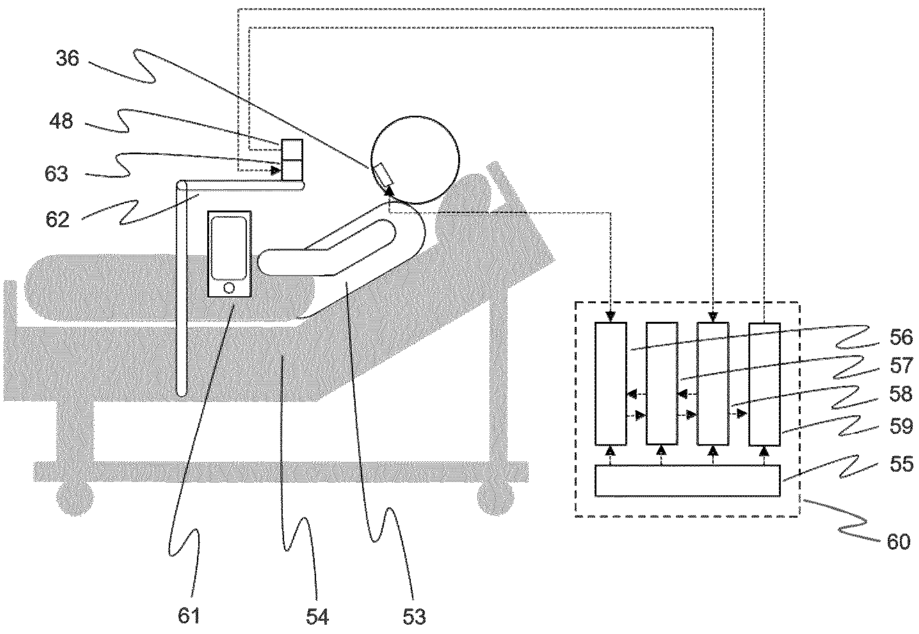
Fig. 8:
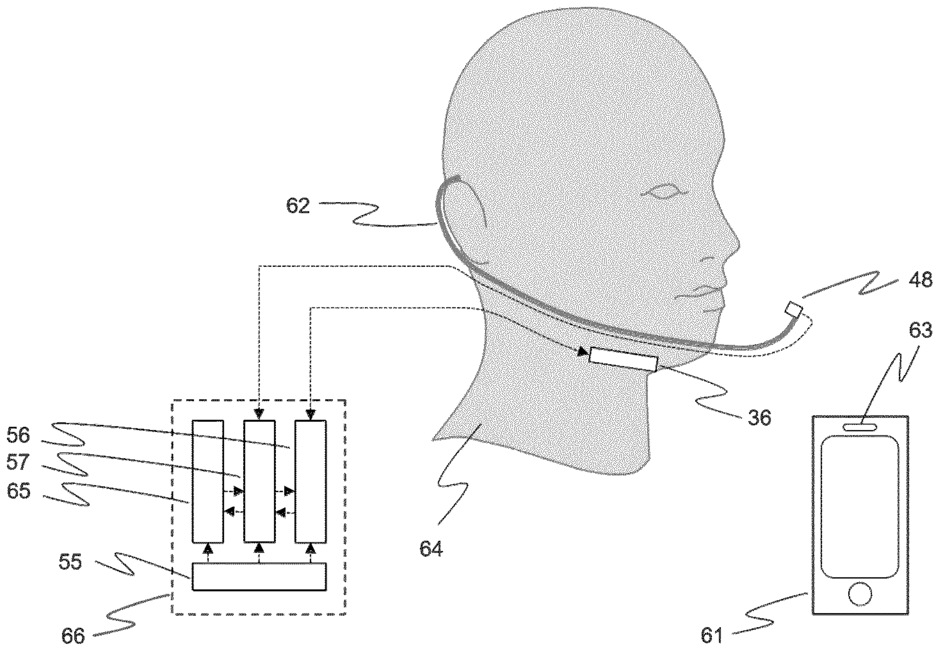

VOICE GRAFTING USING MACHINE LEARNING

TECHNICAL FIELD

Various examples of the invention generally relate to techniques for creating an artificial voice for a patient with missing or impaired phonation but at least residual articulation function.

BACKGROUND

Voice disorders are known to affect 3% to 9% of the population in developed countries and manifest themselves in a range of symptoms collectively known as dysphonia: from hoarseness to a weak or distorted voice to a complete loss of voice, referred to as aphonia. Voice disorders can be functional or organic in origin. Organic voice disorders can be further classified as either structural or neurogenic. This invention deals primarily with severe structural dysphonia and aphonia, but its uses are not limited to these conditions.

In OECD countries, an estimated 60,000 patients per year cannot speak while they are on longer-term mechanical ventilation involving a tracheostomy, and an estimated 12,000 patients per year lose their voice permanently after throat cancer surgery with a partial or total laryngectomy, and an estimated 4,000 thyroid surgeries per year result in severe and lasting speaking problems. Dysphonia or aphonia after thyroid surgery is typically due to vocal fold paresis, most often caused by damage to a recurrent laryngeal nerve.

FIG. 1 shows the main parts of the anatomy of the human voice organs. In technical terms, the human voice is commonly described by the so-called source-filter model. The lungs, the trachea (3), and the larynx (4) together form the source (1). Air is compressed in the lungs and travels upward through the trachea to the larynx. Inside the larynx, the vocal folds (4*a*)—colloquially known as "vocal cords"—form the glottis aperture. Lanryngeal muscles keep the vocal folds under tension by exerting a force via the arytenoid cartilages. For voiced speech, the tracheal pressure and the tension of the vocal folds cause them to periodically open and close, creating an acoustic oscillation, a sound wave. This sound wave is acoustically filtered by the time-varying shape of the vocal tract (2), consisting of the pharynx (6), oral cavity (8), and nasal cavity (12), before being emitted from the mouth and nostrils (13).

Speech production thereby consists of the process of phonation, in technical terms the excitation of an acoustic oscillation by the vocal folds, and articulation, or filtering of the sound spectrum by the time-varying shape the vocal tract. Shaping of the vocal tract is done with the velum (7), which opens or closes off the nasal cavity, the tongue (9), the upper (10*a*) and lower teeth (10*b*), as well as the upper (11*a*) and lower lip (11*b*).

Different situations leading to a partial or complete loss of phonation are shown schematically in FIG. 2. Patients on longer-term mechanical ventilation (FIG. 2) typically undergo a tracheostomy (17), to avoid the side-effects of intubation through the nose or the mouth. A cannula (17*a*) is inserted through an artificial opening of the trachea. Typically, an inflatable cuff (17*b*) is used to form a tight seal inside the trachea. This keeps the exhaled air from flowing through the larynx, preventing phonation. After total laryngectomy (FIG. 2*b*), a permanent opening of the trachea (3), known as a tracheostoma (18), is created, and the esophagus (14) and pharynx are surgically separated from the airway. This situation also prevents physiologic phonation. Thyroidectomy (FIG. 2*c*) can result in injury to one or both of the two recurrent laryngeal nerves (16) which are anatomically very close to the thyroid (15). Laryngeal nerve injury (16*a*) can partially or completely immobilize the vocal folds, impairing or eliminating phonation. It is important to note that in each of these situations described here, the mechanism of phonation is disabled, while the articulation function is not impaired.

Current state-of-the art options for voice rehabilitation are limited. They include:

- Tracheoesophageal puncture, shown in FIG. 3*a*. In laryngectomized patients, a tracheoesophageal puncture (TEP) creates an opening between the trachea and the esophagus, in which a one-way valve, sometimes referred to as a voice prosthesis, is inserted (20). By covering the tracheostoma with a finger (21), patients can re-direct the exhaled air flow through the vocal tract where it causes mechanical vibrations (22), enabling them to speak with a somewhat distorted pseudo-voice.
- Esophageal speech, visualized schematically in FIG. 3*b*. Without a TEP, laryngectomees can practice the so-called esophageal speech, which uses air that is first swallowed and then re-emitted ("burped") from the esophagus to create mechanical vibrations (22). Esophageal speech often sounds unnatural and can be difficult to understand.
- Electrolarynx, or artificial larynx, shown in FIG. 3*c*. An electrolarynx (23) is an electromechanical oscillator, emulating the function of the vocal folds. Mechanical vibrations (22) are applied on the outside of the vocal tract under the chin, or inside the mouth via an oral tube. The electrolarynx is activated with a manual switch. It tends to result in monotone, "mechanical" sounding speech.
- Phonosurgery. In cases of unilateral paresis, phonosurgery attempts to adjust the immobilized vocal fold to a position that achieves the best compromise between glottis closure, which is needed for the ability to phonate, and sufficient air flow for breathing. This can be achieved with sutures, laser surgery, or filler materials such as silicone or hyaluronic acid.
- Speech therapy. Speech therapists specialize in training patients' residual vocal capabilities through voice exercises. Many recurrent nerve injuries are transient, and the effects of a one-sided paresis can often be compensated by strengthening the contra-lateral vocal fold.

In many cases, none of these options are a satisfying solution. Patients on mechanical ventilation and patients with completely immobilized vocal folds or a surgically removed larynx often recover a rudimentary ability to communicate, albeit with difficulty and/or with a severely distorted voice.

Voicelessness and impaired communication have serious effects on patients, relatives, and caregivers' ability to care for a patient. Voicelessness and inability to communicate verbally have been associated with poor sleep, stress, anxiety, depression, social withdrawal, and reduced motivation of patients to participate in their care.

Next, an overview of related prior work is given:

While the available therapeutic options for voiceless patients are limited, a number of approaches to problem of recognizing speech from measurements of the vocal tract, the larynx, the neck and facial musculature, and the lip and facial movements have been described in the literature. The field of research concerned with speech recognition without acoustic voice input is sometimes referred to as "silent speech" research. Below, key results of silent speech research as the relate to this invention and the main differences are summarized.

Radar sensing: Holzrichter et al. at Lawrence Livermore National Laboratory have developed a range of ideas around the recognition of speech from radar signals in combination with an acoustic microphone. Their fundamental patents date back to 1996. While Holzrichter's focus is on improving speech recognition from healthy speakers, he does mention prosthetic applications in passing, without describing them in detail. However, his primary objective is measurement of the vocal excitation function, i.e. vocal fold motion, rather than the vocal tract configuration—which is fundamentally different from the objective of techniques described herein. Accordingly, all of the described embodiments by Holzrichter et al. require at least partial phonation. See, e.g., Ng, Lawrence C., John F. Holzrichter, and P. E. Larson. *Low Bandwidth Vocoding Using EM Sensor and Acoustic Signal Processing*. No. UCRL-JC-145934. Lawrence Livermore National Lab., CA (US), 2001. Further see: Holzrichter, J. F. *New ideas for speech recognition and related technologies*. No. UCRL-ID-120310. Lawrence Livermore National Lab. (LLNL), Livermore, CA (United States), 2002. Further, see Holzrichter, John F., Lawrence C. Ng, and John Chang. "Real-time speech masking using electromagnetic-wave acoustic sensors." *The Journal of the Acoustical Society of America* 134.5 (2013): 4237-4237. Also, see Jiao, Mingke, et al. "A novel radar sensor for the non-contact detection of speech signals." *Sensors* 10.5 (2010): 4622-4633. See Li, Sheng, et al. "A 94-GHz millimeter-wave sensor for speech signal acquisition." *Sensors* 13.11 (2013): 14248-14260.

Recently, Birkholz et al. have demonstrated silent phoneme recognition with microwave signals using two antennas attached on test subjects' cheek and below the chin. Measuring time-varying reflection and transmission spectra in the frequency range of 2-12 GHz they achieved phoneme recognition rates in the range of 85% to 93% for a limited set of 25 phonemes. See, e.g., Birkholz, Peter, et al. "Non-invasive silent phoneme recognition using microwave signals." *IEEE/ACM Transactions on Audio, Speech, and Language Processing* 26.12 (2018): 2404-2411.

Ultrasound: Ultrasound imaging has been studied as input for speech recognition and synthesis, sometimes in combination with optical imaging of the lips. See, e.g., Hueber, Thomas, et al. "Eigentongue feature extraction for an ultrasound-based silent speech interface." 2007 *IEEE International Conference on Acoustics, Speech and Signal Processing-ICASSP'*07. Vol. 1. IEEE, 2007; or Hueber, Thomas, et al. "Development of a silent speech interface driven by ultrasound and optical images of the tongue and lips." *Speech Communication* 52.4 (2010): 288-300; or Hueber T. Speech Synthesis from ultrasound and optical images of the speaker's vocal tract. Available at: https://www.neurones.espci.fr/ouisper/doc/report_hueber_ouisper.pdf. Accessed Oct. 16, 2018. Hueber, Denby et al. have filed patent applications for a speech recognition and reconstruction device consisting of a wearable ultrasound transducer and a way of tracking its location relative to the patient's head via mechanical means or a 3-axis accelerometer. They also describe image processing methods to extract tongue profiles from two-dimensional ultrasound images. See Denby, Bruce, and Maureen Stone. "Speech synthesis from real time ultrasound images of the tongue." 2004 *IEEE International Conference on Acoustics, Speech, and Signal Processing*. Vol. 1. IEEE, 2004; or Denby, Bruce, et al. "Prospects for a silent speech interface using ultrasound imaging." 2006 *IEEE International Conference on Acoustics Speech and Signal Processing Proceedings*. Vol. 1. IEEE, 2006.

Hueber's paper "Speech Synthesis from ultrasound and optical images of the speaker's vocal tract" describes the use of machine learning (sometimes also referred to as artificial intelligence) to translate vocal tract configurations into voice output. The concepts Hueber and Denby describe in their publications are limited to ultrasound imaging of the tongue and camera imaging of the lips, and always use ultrasound images as an intermediate processing step. Their experiments aimed at building a "silent speech interface" led Hueber et al. to the conclusion that "with some 60% of phones correctly identified [ . . . ], the system is not able to systematically provide an intelligible synthesis".

McLoughlin and Song have used low-frequency ultrasound in a 20 to 24 kHz band to sense voice activity via the detection of the mouth state, i.e. the opening and closing of a test subject's lips. Even though their system provided only binary voice activity output, it required subject specific training of the detection algorithm. See, e.g., McLoughlin, Ian Vince. "The use of low-frequency ultrasound for voice activity detection." *Fifteenth Annual Conference of the International Speech Communication Association*. 2014; and McLoughlin, Ian, and Yan Song. "Low frequency ultrasonic voice activity detection using convolutional neural networks." *Sixteenth Annual Conference of the International Speech Communication Association*. 2015.

Lip and facial video: Zisserman's group at the University of Oxford, Shillingford et al., and Makino et al. have demonstrated combined audio-visual speech recognition using facial video in combination with audio speech data as input to deep neural network algorithms. While their results show that video data can be used to enhance the reliability of audio speech recognition, the approaches they describe are limited to recognizing the speech of healthy subjects with audible speech output. See e.g. Chung, Joon Son, and Zisserman, Andrew. "Lip Reading in Profile." *British Machine Vision Association and Society for Pattern Recognition*. 2017; Shillingford, Brendan, et al. "Large-Scale Visual Speech Recognition". *INTERSPEECH*. 2019; and Makino, Takaki, et al. "Recurrent Neural Network Transducer for Audio-Visual Speech Recognition". *IEEE Automatic Speech Recognition and Understanding Workshop*. 2019.

Surface electromyography: Surface EMG of the neck and face has been tested for Human-Computer Interfaces (HCI), particularly in so-called Augmentative and Alternative Communication (AAC) for people with severe motor disabilities, e.g. due to spinal cord injury or amyotrophic lateral sclerosis (ALS), a motor neuron disease. Stepp's group at Boston University uses surface EMG as input for AAC interfaces: EMG signals from the neck or facial musculature are picked up and allow the patient to move a cursor on a screen. This can be used to design a "phonemic interface" in which the patient painstakingly chooses individual phonemes that are assembled into speech output. Among other aspects, this differs from this invention in that it is not real time. See, e.g., Janke, Matthias, and Lorenz Diener. "EMG-to-speech: Direct generation of speech from facial electromyographic signals." *IEEE/ACM Transactions on Audio, Speech, and Language Processing* 25.12 (2017): 2375-2385; or Denby, Bruce, et al. "Silent speech interfaces." *Speech Communication* 52.4 (2010): 270-287; or Wand, Michael, et al. "Array-based Electromyographic Silent Speech Interface." *BIOSIGNALS*. 2013. Further, see Stepp, Cara E. "Surface electromyography for speech and swallowing systems: measurement, analysis, and interpretation." *Journal of Speech, Language, and Hearing Research* (2012); also see Hands, Gabrielle L., and Cara E. Stepp. "Effect of Age on Human-Computer Interface Control Via Neck Electromyography." *Interacting with computers* 28.1 (2016): 47-54; also see Cler, Meredith J., et al. "Surface electromyographic control of speech synthesis." 2014 36*th Annual International Conference of the IEEE Engineering in Medicine and Biology Society*. IEEE, 201.

Speech synthesis from surface EMG signals has been tried, albeit with limited success. Meltzner at al. succeeded in speech recognition in a 65-word vocabulary with a success rate of 86.7% for silent speech in healthy subjects. Meltzner's DARPA-funded study used an HMM for speech recognition from surface EMG signals. The main differences to this invention are that it appears to be limited to a small vocabulary, and does not include a versatile speech synthesis stage. See Meltzner, Geoffrey S., et al. "Speech recognition for vocalized and subvocal modes of production using surface EMG signals from the neck and face." *Ninth Annual Conference of the International Speech Communication Association.* 2008.

Electrocorticography: Recently, two groups have demonstrated rudimentary speech recognition from brain signals via electrocorticography. Since this technique required electrodes invasively placed inside the cerebral cortex, it is only conceivable for severely disabled patients, such as advanced-stage ALS patients, for whom the risk of such a procedure could be justified. Moses et al. showed rudimentary speech recognition within a limited vocabulary using electrocorticography in combination with a context sensitive machine learning approach. Akbari et al. also added machine learning based speech synthesis to reconstruct audible speech within a very limited vocabulary. Both approached differ from this invention in their highly invasive nature. See, e.g., Akbari, Hassan, et al. "Towards reconstructing intelligible speech from the human auditory cortex." *Scientific reports* 9.1 (2019): 1-12; and Moses, David A., et al. "Real-time decoding of question-and-answer speech dialogue using human cortical activity." *Nature communications* 10.1 (2019): 1-14.

The following patent publications are known: DE 202004010342 U1; EP 2577552 B1; U.S. Pat. Nos. 5,729,694; 6,006,175; 7,162.415 B2; 7,191,105 B2; US 2012/0053931 A1.

SUMMARY

It is an objective of the techniques described herein to restore in real time natural-sounding speech for patients who have impaired or missing phonation, but have retained at least a partial ability to articulate. This includes, but is not limited to, the three conditions described above: mechanical ventilation, laryngectomy, and recurrent nerve paresis.

A further objective of the techniques described herein is to match the restored voice to desired voice characteristics for a particular patient, for example, by matching the restored voice closely to the patient's voice prior to impairment. While in intensive care unit (ICU) settings, a solution could be a stationary bedside unit, for most other settings, it is an additional objective to provide a solution that is wearable, light-weight, and unobtrusive.

This need is met by the features of the independent claims. The features of the dependent claims define embodiments.

Unlike prostheses that attempt to restore, or mechanically substitute, a patient's ability to phonate, i.e. to produce an acoustic wave that is shaped into speech in the vocal tract, the approach of the techniques described herein is to measure the time-varying physical configuration of the vocal tract, i.e. to characterize the patient's attempted articulation, numerically synthesize a speech waveform from it in real time, and output this waveform as an acoustic wave via a loudspeaker.

Many of the techniques described herein can employ a process labeled "voice grafting" hereinafter. Voice grafting can be understood in terms of the source-filter model of speech production as follows: For a patient who has partially or completely lost the ability to phonate, but retained at least a partial ability to articulate, the techniques described herein computationally "graft" the patient's time varying filter function, i.e. articulation, onto a source function, i.e. phonation, which is based on the speech output of one or more healthy speakers, in order to synthesize natural sounding speech in real time. Real time can correspond to a processing delay of less than 0.5 seconds, optionally of less than 50 ms.

As a general rule, some of the examples described herein pertain to a training of a machine learning algorithm (i.e., creating respective training data and executing the training based on the training data); and some further examples described herein relate to inference provided by the trained machine learning algorithm. Sometimes, the methods can be limited to training; and sometimes, the methods can be limited to inference. It is also possible to combine training and inference.

Regarding the training: A respective method includes training a machine learning algorithm based on, firstly, one or more reference audio signals. The reference audio signals include a speech output of a reference text. The machine learning algorithm is, secondly, trained based on one or more vocal-tract signals. The one or more vocal-tract signals are associated with an articulation of the reference text by a patient.

In other words, it is possible to record the one or more reference audio signals as the acoustic output of one or more healthy speakers reading the reference text. The vocal-tract signal of the patient corresponds to the patient articulating the same reference text.

Training is performed in a training phase. After the training phase is completed, an inference phase commences. In the inference phase, it would then be possible to receive one or more further vocal-tract signals of the patient and convert the one or more further vocal-tract signals into an associated speech output based on the machine learning algorithm. Such further signals can be referred to as "live signals", because they are received after training, without any ground truth (such as the reference text) being available.

Such techniques as described above and below help to provide a voice grafting that is based on machine learning techniques. The techniques can be implemented in a mobile computing device (also referred to as user device). Accordingly, the voice grafting can be implemented in a variable, lightweight, and unobtrusive manner. In other examples, e.g., in an intensive care unit setting, it would also be possible to implement on a mobile computing device that is stationary bedside.

The techniques described herein can be implemented by methods, devices, systems, or computer programs/computer-program products/and computer-readable storage media that execute respective program code.

It is to be understood that the features mentioned above and those yet to be explained below may be used not only in the respective combinations indicated, but also in other combinations or in isolation without departing from the scope of the invention.

BRIEF DESCRIPTION OF THE DRAWINGS

FIG. 7 schematically illustrates a voice prosthesis employing radar and video sensors for bedridden patients according to various examples.

FIG. 8 schematically illustrates a voice prosthesis employing radar and video sensors for mobile patients according to various examples.

DETAILED DESCRIPTION OF EMBODIMENTS

Hereinafter, techniques of generating a speech output based on a residual articulation of the patient (voice grafting) are described. Various techniques are based on the finding that prior-art implementations of speech rehabilitation face certain restrictions and drawbacks. For example, for many patients they do not achieve the objective of restoring natural-sounding speech. Esophageal speech and speaking with the help of a speaking valve, voice prosthesis, or electrolarynx are difficult to learn for some patients and often results in distorted, unnatural speech. The need to hold and activate an electrolarynx device or cover a tracheostoma or valve opening with a finger makes these solutions cumbersome and obtrusive. In-dwelling prostheses also carry the risk of fungal infections.

For example, details with respect to a speak valve are described in: Passy, Victor, et al. "Passy-Muir tracheostomy speaking valve on ventilator-dependent patients." The Laryngoscope 103.6 (1993): 653-658. Also, see Kress, P., et al. "Are modern voice prostheses better? A lifetime comparison of 749 voice prostheses." European Archives of Oto-Rhino-Laryngology 271.1 (2014): 133-140.

For example, details with respect to a speak valve are described in: Passy, Victor, et al. "Passy-Muir tracheostomy speaking valve on ventilator-dependent patients." *The Laryngoscope* 103.6 (1993): 653-658. Also, see Kress, P., et al. "Are modern voice prostheses better? A lifetime comparison of 749 voice prostheses." *European Archives of Oto-Rhino-Laryngology* 271.1 (2014): 133-140.

An overview of traditional voice prostheses is provided by: Reutter, Sabine. *Prothetische Stimmrehabilitation nach totaler Kehlkopfentfernung-eine historische Abhandlung seit Billroth* (1873). Diss. Universität Ulm, 2008.

Figure 4:
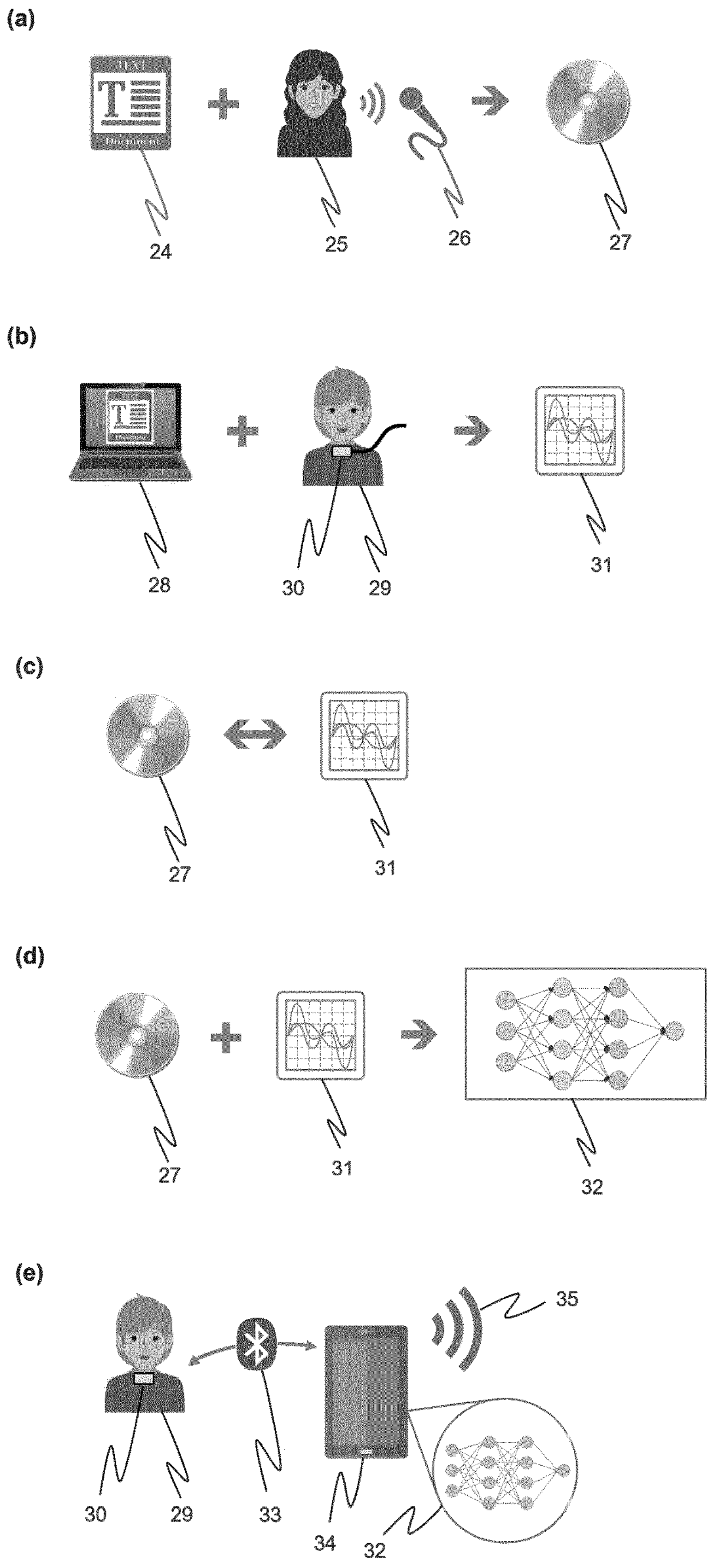
FIG. 4 is a flow-schematic of a method according to various examples; (4*a*) Step 1*a*: Creating audio training data; (4*b*) step 1*b*: Creating vocal tract training data; (4*c*) step 1*c*: synchronizing audio and vocal tract training data; (4*d*) step 2: training the algorithm; (4*e*): step 3: using the voice prosthesis.

Many different implementations of the voice grafting are possible. One implementation is shown schematically in FIG. 4. It includes three steps, as follows.

Step 1: Creating training data, i.e., training phase. A healthy speaker (25) providing the "target voice" reads a sample text (24) (also labelled reference text) out loud, while the voice output is recorded with a microphone (26). This can create one or more reference audio signals, or simply audio training data. The resulting audio training data (27), including the text and its audio recording, can be thought of as an "audio book"; in fact, it can also be an existing audio book recording or any other available speech corpus. (Step 1 *a*, FIG. 4 *a*).

The same text is then "read" by a patient with impaired phonation (29), while signals characterizing the patient's time-varying vocal tract configuration, i.e. the articulation, are recorded with suitable sensors (30), yielding vocal tract training data (31). If the patient is completely aphonic, "reading" the text here means silently "mouthing" it. To record the articulation, various options exist. For example, the patient's vocal tract is probed using electromagnetic and/or acoustic waves, and backscattered and/or transmitted waves are measured. Together, the measurement setup can be referred to as "vocal tract sensors" and to the measured signals as "vocal tract signals". (Step 1*b*, FIG. 4*b*).

A third aspect of creating training data is a way of synchronizing the audio training data (27) and the vocal tract training data (31). This can be done either during the data recording, or afterwards by selectively speeding up or slowing down the recorded signals for synchronization. (Step 1*c*, FIG. 4*c*).

Step 2: Training the algorithm (FIG. 4*d*), i.e., training phase. The second step in the overall process is training a machine learning algorithm, to transform vocal tract signals into the acoustic waveform of acoustic speech output. The audio training data (27) and the vocal tract training data (31) are used to train the machine learning algorithm (32) such as a deep neural net to transform vocal tract data into acoustic speech output.

Thus, as a general rule, a method includes training a machine learning algorithm based on, firstly, one or more reference audio signals. The reference audio signals include a speech output of a reference text. The machine learning algorithm is, secondly, trained based on one or more vocal-tract signals. The one or more vocal-tract signals are associated with an articulation of the reference text by a patient.

The training of the machine learning algorithm according to step 1 and step 2 is distinct from inference using the trained machine learning algorithm. Inference is described in connection with step 3 below.

Step 3: Using the voice prosthesis (FIG. 4*e*), inference phase. The third step is using the trained machine learning algorithm to transform measurements of the impaired patient's vocal tract signals into acoustic speech output in real time in a voice prosthesis system. Here, one or more live vocal-tract signals can be acquired using one or more sensors associated with at least one mobile computing device. In this step, the patient (29) typically wears the same or similar vocal tract sensor configuration (30) that was used in creating the training data. For example, the measured vocal tract signals are transmitted to a mobile computing device (34) via a wireless connection (33) and fed into the trained machine learning algorithm (32) to be converted to an acoustic speech waveform in real time, i.e., one or more live audio signals are generated by the machine-learning algorithm. The acoustic speech waveform (35) is output using the device loudspeaker.

Thus, as a general rule, a corresponding method can include receiving one or more live vocal-tract signals of the patient and then convert the one or more live vocal-tract signals into associated one or more live audio signals including speech output, based on the machine learning algorithm.

For each step described above, a wide range of implementations is possible, which will be described below.

Step 1*a*: Creating the audio training data. The audio training data representing the "healthy voice" can come from a range of different sources. In the most straightforward implementation it is the voice of a single healthy speaker. The training data set can also come from multiple speakers. In one implementation, a library of recordings of speakers with different vocal characteristics could be used. In the training step, training data of a matching target voice would be chosen for the impaired patient. The matching could happen based on gender, age, pitch, accent, dialect, and other characteristics, e.g., defined by a respective patient dataset.

Thus, as a general rule, it would be possible to train multiple configurations of the machine learning algorithm, using multiple speech outputs having various speech characteristics and/or using multiple articulations of the reference text having various articulation.

The method could further include selecting a configuration from the plurality of configurations of the machine learning algorithm based on a patient data set indicative of demographic and phonetic characteristics of the patient.

The speech characteristics may specify characteristics of the speech output. Example speech characteristics include: pitch; gender; accent; age; etc. Accordingly, it would be possible that the known body of text has been pre-recorded with a plurality of healthy speakers with different voice characteristics. The articulation characteristic can specify characteristics of the articulation and/or its sensing. Example articulation characteristics include: type of vocal tract impairment; type of sensor technology used for recording the one or more vocal-tract signals; etc.

The patient dataset may specify speech characteristics of the patient and/or articulation characteristics of the patient. Thereby, a tailored configuration of the machine learning algorithm can be selected, providing an appropriate speech output based on an the specific articulation of the patient.

The audio training data can either be custom-generated for a specific patient, or serve for a range of patients, or it can be a pre-existing database of recordings. Several such databases are available, for example through the Bavarian Archive for Speech Signals or through OpenSLR. A custom voice sample could also be matched to the types of conversations the patient is likely to have. This may be especially advantageous with very severely handicapped patients for whom the therapy goal is to reliably communicate with a limited vocabulary.

A preferred voice sample would be of the patient's own voice. This requires a recording of a sufficient body of text of the patient's original voice prior to injury or surgery, to be used as a training data set for the algorithm. For example, in cases of total laryngectomy it is conceivable that the patient's voice gets extensively recorded before the surgery. In such an implementation, the recording of the audio training data (Step 1*a*) and the recording of the corresponding vocal tract signals (Step 1*b*) can occur concurrently.

Thus, it would also be possible that the speech output of the reference text, included in the one or more reference audio signals, is provided by the patient prior to the impairment. Accordingly, the healthy speaker could be identical with the impaired patient, prior to the impairment. Thereby, a particular accurate training of the machine learning algorithm and a unique speech output tailored to the patient can be provided.

Step 1*b*: Creating the vocal tract training data. The vocal tract training data can also come from a range of different sources. In the most straightforward implementation it comes from a single person, the same impaired patient who will use the voice prosthesis in Step 3. The vocal tract signal training data can also come from multiple persons, who do not all have to be impaired patients. For example, the training can be performed in two steps: a first training step can train the machine learning algorithm with a large body of training data consisting of audio data from multiple healthy speakers and vocal tract data from multiple healthy and/or impaired persons. A second training step can then re-train the network with a smaller body of training data containing the vocal tract signals of the impaired patient who will use the voice prosthesis.

Thus, as a general rule, it would be possible that the machine learning algorithm is pre-trained based on a plurality of healthy speakers and impaired patients, and then re-trained for a particular impaired patient. I.e., it would be possible that the one or more vocal-tract signals based on which the training of the machine learning algorithm is executed are at least partially associated with the patient (and optionally also partially associated with one or more other persons, as already described above).

Figure 5:
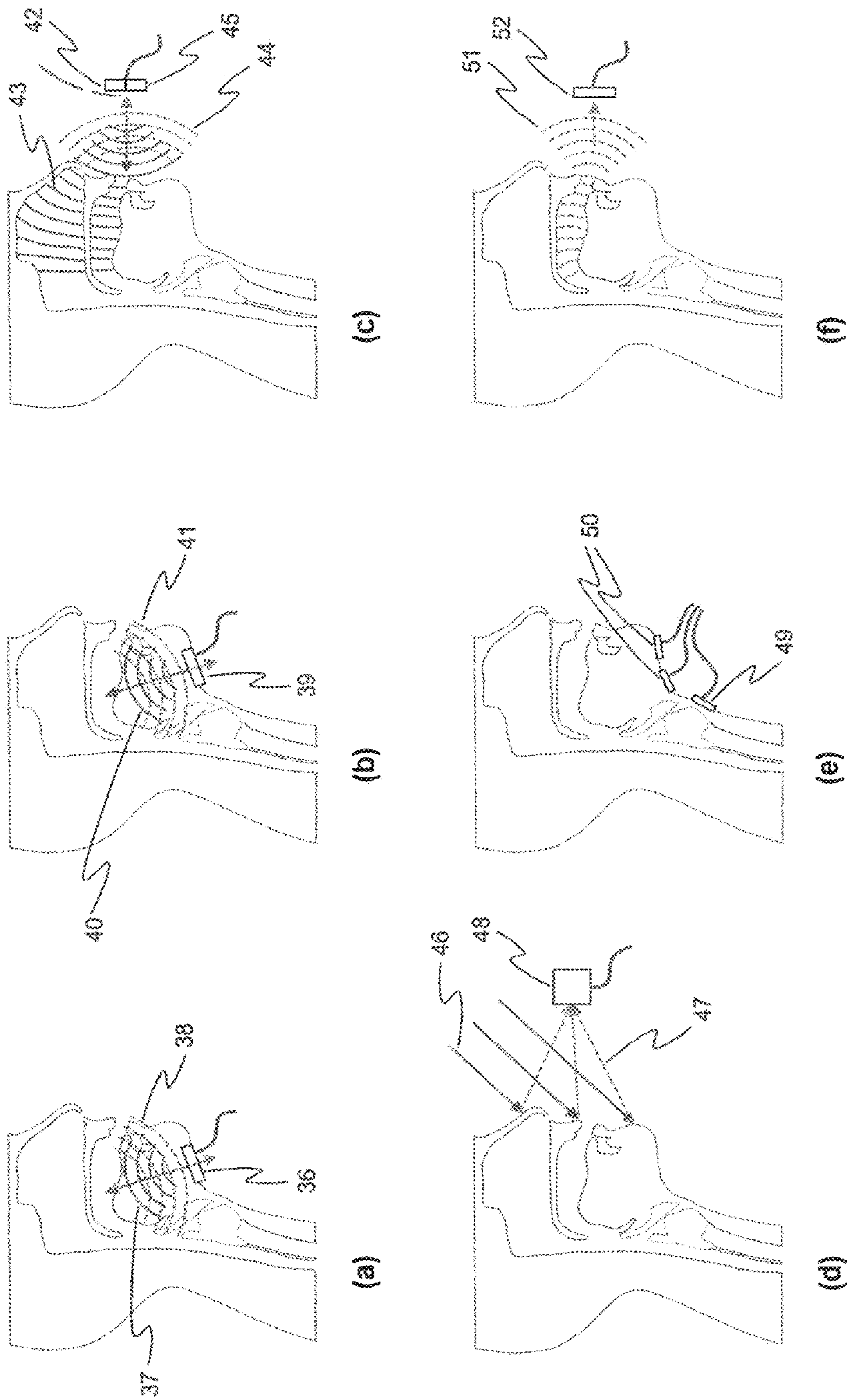
FIG. 5 schematically illustrates different implementation options for vocal tract sensors. (a) microwave radar sensing; (b) ultrasound sensing; (c) low-frequency ultrasound; (d) lip and facial camera; (e) surface electromyography; (f) acoustic microphone.

To measure articulatory movement, a range of different electromagnetic or acoustic sensors, or both, can be used to probe the vocal tract and characterize its time-varying shape, as shown schematically in FIG. 5. As a general rule, sensors could be any, or a combination, of the following: radar transceivers (including phased arrays), radar reflectors (including active and passive), ultrasound transceivers (including phased arrays), ultrasound reflectors (including active and passive), cameras, surface electromyography electrodes, and/or microphones.

An example for electromagnetic sensors includes radar transceivers, operating in the radio frequency range—e.g., the microwave range—of the electromagnetic spectrum (FIG. 5*a*). One or more radar antennas (36) can be placed externally near the subject's vocal tract, e.g., at the cheeks or under the mandible. At frequencies between 1 kHz and 12 GHz emitted electromagnetic waves (37) (optionally at frequencies between 1 and 12 GHz) will penetrate several centimeters to tens of centimeters into tissue. The waves backscattered and transmitted or otherwise influenced by tissue (38) are detected with the same or a dedicated set of antennas used for emission. At the extremely low average milliwatt power levels required, they are safe for continuous use on humans. The electromagnetic signal can be emitted into a broad beam and detected either with a single antenna or in a spatially or angularly resolved manner, with a phased array antenna configuration. A multiple input, multiple output (MIMO) configuration can be employed as well. The received, time-varying electromagnetic signal encodes information about the time-varying shape of the vocal tract which can be used in the machine learning algorithm. In the following, the term "radar" and "radar signal" is used in the generalized form introduced above.

An example of acoustic waves sensors are ultrasound transceivers as used, for example, in medical imaging (FIG. 5*b*). An ultrasound transducer (39) is placed in contact with the patients skin, e.g. under the mandible. In the frequency range of 1 to 5 MHz, ultrasound penetrates the pertinent tissues well and can also be operated safely in a continuous way. Emitted ultrasound waves (40) are backscattered by tissue, and the backscattered waves (41) are detected with the transducer (39). Ultrasound sensing can be used either in a two- or three-dimensional imaging mode, for example using a phased array transducer, or in a non-imaging mode, where features of the backscattered ultrasound signals are directly used in the machine learning algorithm. Ultra-compact, chip-based phased-array ultrasound transceivers are available, for example, for endoscopic applications. The time-varying backscattered ultrasound wave encodes information about the time-varying shape of the vocal tract which can be used in the machine learning algorithm.

Another possibility for acoustic sensing of the vocal tract configuration is using low-frequency ultrasound waves (FIG. 5*c*) in the range of 20 to 100 kHz. An ultrasound loudspeaker (42) in front of the subject's mouth can be used to emit low-frequency ultrasound waves (43) which penetrate the vocal tract. The reflected ultrasound signal (44) can be detected using an ultrasound microphone (45) in front of the subject's mouth. The frequency-dependent sound wave reflection coefficient from the speaker to the microphone encodes information about the time-varying shape of the vocal tract which can be used in the machine learning algorithm.

Further, to deal with specific challenges it can be advantageous to introduce an auxiliary sensing modality. Multi-modality sensing (sometimes referred to as sensor fusion) can reduce the effects of inter-subject and inter-session variability by introducing additional redundancy into the measured signals. In addition, some characteristics of human speech such as pitch, volume, and timbre—referred to by linguists as prosodic variables—are not explicitly encoded in the vocal tract but are a result of the phonation process. To reconstruct prosody, multi-modality sensing may also be advantageous. The type of auxiliary sensing modality to be used in conjunction depends on the type of impairment causing the patient's dysphonia or aphonia. It is possible to use combinations of such auxiliary sensing modalities. In particular, it would be possible that the machine learning algorithm accepts multiple types of speech-related sensor signals as inputs, e.g., acquired using different sensors and/or monitoring different physical observables, as explained above.

An example of an electromagnetic auxiliary sensing modality is a video camera recording the motion of the lips and facial features during speech (FIG. 5*d*). The video camera (48) captures light reflected (47) scattered off the patient's face under ambient or emitted illumination (46). As can be seen from some deaf people's ability to "lip read", lip and facial movements are a rich source of information about what is being said and how. Also, a camera can be realized in a compact, light-weight, unobtrusive setup. Since in most of the types of impairments considered here, lip and facial movements remain unimpaired, a video camera is thus a preferred implementation for an auxiliary sensing modality. Also, multiple video cameras or depth-sensing cameras, such as cameras using time-of-flight technology, can be used in order to reconstruct three-dimensional facial geometry.

Another example of an electromagnetic auxiliary sensing modality is surface electromyography (EMG) (FIG. 5*e*). Surface EMG can measure the action potentials of the musculature involved in speech production, providing complementary information to the vocal tract configuration, e.g. by encoding intended loudness. A combination of surface EMG sensors for the extrinsic laryngeal musculature (49) and the neck and facial musculature (50) can be used. Surface EMG can be particularly useful in cases where the extrinsic laryngeal musculature is present and active.

An example of an acoustic auxiliary sensing modality is an acoustic microphone (FIG. 5 *f*). A microphone as a complementary source of information about articulation, and possibly residual phonation, makes sense in all cases of impairment where a residual voice or a whisper is present. The microphone (52) picks up the acoustic waves associated with the residual acoustic voice signal (51). Whispering requires air flow through the vocal tract, but does not require phonation, i.e. vocal fold motion. Like a video camera, a microphone can be compact, light-weight, and unobtrusive. It can be positioned on the outside of the patient's throat, under the mandible, or in front of the mouth. A microphone can also be used in combination with a lip and facial camera, for example on the same headset cantilever in front of the patient's mouth.

In situations where the impaired patient has retained significant residual voice, for example a clearly articulated whisper or residual phonation, a microphone as an acoustic sensing modality in combination with a lip and facial camera as an auxiliary sensing modality can be advantageous.

Step 1*c*: Synchronizing audio and the vocal tract training data. As a general rule, the method may further include synchronizing a timing of the one or more reference audio signals with a further timing of the one or more vocal-tract signals. By synchronizing the timings, an accurate training of the machine learning algorithm is enabled. The timing of a signal can correspond to the duration between corresponding information content. For example, the timing of the one or more reference audio signals may be characterized by the time duration required to cover a certain fraction of the reference text by the speech output; similarly, the further timing of the one or more vocal-tract signals can correspond to the time duration required to cover a certain fraction of the reference text by the articulation.

Time synchronization between the audio training data and the vocal tract training data can be achieved in a variety of different ways, either during recording or afterwards. If the two data sets are acquired at the same time from the same subject, synchronization is achieved automatically.

If the two data sets are acquired consecutively, synchronization can be accomplished by providing visual or auditory cues to the subject recording the vocal tract training data. This can be done, for example, by displaying the sample text to be recorded on a screen, with a cursor moving along at the speed of the audio recording of the target voice, or by quietly playing back that recording. In each case, the subject whose vocal tract signals are recorded aims to match the given speed. Thus, for example, it would be possible to control a human-machine-interface (HMI) to provide temporal guidance to the patient when articulating the reference text in accordance with the timing of the one or more reference audio signals. For example, it would be possible that the synchronization is achieved by providing optical or acoustic cues to the impaired patient while the vocal-tract signals are being recorded.

Alternatively or additionally, it would also be possible that said synchronizing includes controlling the HMI to obtain a temporal guidance from the patient when articulating the reference text. For example, the impaired patient could provide synchronization information by pointing at the part of the text being articulated, while the one or more vocal-tract signals are being recorded. Gesture detection or eye tracking may be employed. The position of an electronic pointer, e.g., mouse curser, could be analyzed. A third approach is to synchronize the audio training data and the vocal tract data computationally after recording, by selectively slowing down or speeding up one of the two data recordings. This requires both data streams to be annotated with timing cues. For the vocal tract signals, the subject recording the training set can provide these timing cues themselves by moving an input device, such as a mouse or a stylus, through the text at the speed of his or her reading. For the audio training data, the timing cues can be generated in a similar way, or by manually annotating the data after recording, or with the help of state-of-the-art speech recognition software. Thus, as a general rule, it would be possible that said synchronizing includes postprocessing at least one of the reference audio signal and a vocal-tract signal by changing a respective timing. In other words, it would be possible that said synchronizing is implemented electronically after recording of the one or more reference audio signals and/or the one or more vocal-tract signals, e.g., by selectively speeding up/accelerating or slowing down/decelerating the one or more reference audio signals and/or the one or more vocal-tract signals.

Step 2: Training the machine learning algorithm. A range of different algorithms commonly used in speech recognition and speech synthesis can be adapted to the task of transforming vocal tract signals into acoustic speech output. The transformation can either be done via intermediate representations of speech, or end-to-end, omitting any explicit intermediate steps. Intermediate representations can be, for example, elements of speech such as phonemes, syllables, or words, or acoustic speech parameters such as mel-frequency cepstral coefficients (MFCCs).

Figure 6:
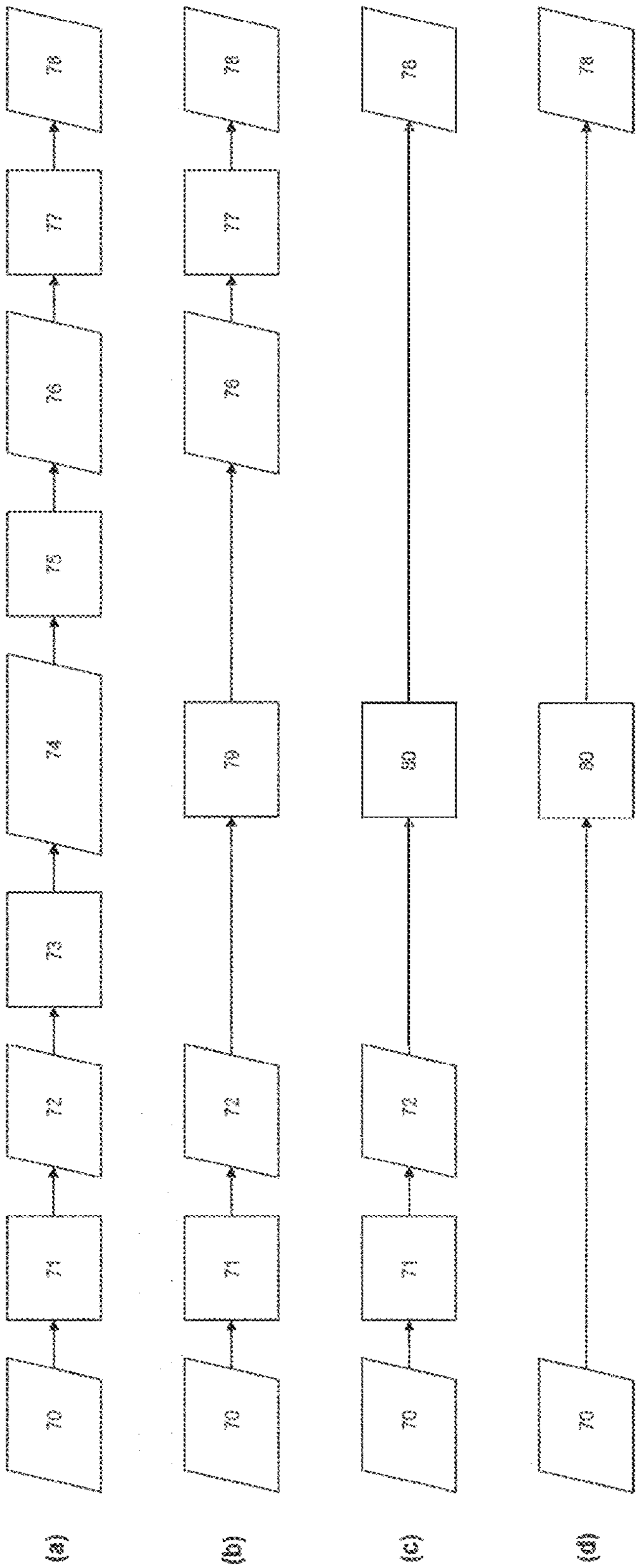
FIG. 6 schematically illustrates flowcharts for multiple implementation options for a machine learning algorithm according to various examples. (a) Uses elements of speech and MFCCs as intermediate representation of speech; (b) uses MFCCs as intermediate representation of speech; (c) is an end-to-end machine learning algorithm using no intermediate representation of speech; and (d) is an end-to-end machine learning algorithm using no explicit pre-processing and no intermediate representation of speech.

Different options for transforming input vocal tract signals into acoustic speech output are illustrated in FIG. 6.

In any case, the input includes one or more the vocal tract signals, e.g., partitioned into a time series of frames (cf. blocks 70). The length of each frame is typically on the order of 5-50 ms, during which the vocal tract configuration can be assumed to be approximately constant. Depending on the type of sensors used, the data in each frame can be received electromagnetic waves or ultrasound signals, an optical image, or an acoustic spectrum.

Through suitable pre-processing (the pre-processing is generally optional, cf. blocks 71), a feature vector can be extracted from each frame. The task of the machine learning algorithm is then to transform the time series of feature vectors (cf. blocks 72), which implicitly encode the vocal tract configuration, into an acoustic waveform representing the speech output.

If elements of speech, such as phonemes, syllables, or words, and MFCCs are used as intermediate representations (cf. block 74), the task can be divided into two subtasks: a speech recognition task (cf. block 73), recognizing the intermediate representation from the time series of feature vectors, and a speech synthesis tasks (cf. block 75), synthesizing an acoustic speech waveform (cf. block 78) from the intermediate representation (FIG. 6*a*). It is possible that block 73 and/or block 75 are implemented by a machine learning algorithm trained as described throughout.

Next, various examples for implementing the machine learning algorithm are described. The recognition task can be accomplished using the types of statistical algorithms commonly used in state-of-the-art speech recognition, such as Hidden Markov Models (HMMs), Gaussian Mixture Models (GMMs), or Deep Neural Networks (DNNs). In each of these cases, a statistical model is created the predict the probabilities that a certain time series of feature vectors corresponds to a certain representation, e.g. a certain phoneme, syllable or word. The probabilities are "learned" during the training process by using the feature vectors corresponding to the vocal tract signals in the training data set and the representations of the corresponding sample text as a statistical sample.

The synthesis task (cf. block 75) can be accomplished using established speech synthesis algorithms. In Unit Selection Synthesis algorithms, elements of speech are selected from a pre-recorded body of elements and are joined together to from speech output. Statistical models such as HMMs and DNNs are now also commonly used to create the acoustic waveform of speech output from representations of speech, such as phonemes, syllables, or words. This can be done via acoustic speech parameters, such as mel-frequency cepstral coefficients as an intermediate step, or directly—as, for example, in Google's WaveNet and Tacotron speech synthesis systems.

If no elements of speech—such as phonemes, syllables, or words—are used as intermediate steps, a machine learning algorithm such as a DNN (cf. block 79) can be trained to transform the series of feature vectors corresponding to the vocal tract signals directly into a representation of the speech output, such as MFCCs (cf. block 76), which are in turn converted to an acoustic speech waveform using acoustic waveform synthesis (cf. block 77-78) (FIG. 6*b*).

If the encoding of the acoustic speech output, e.g. in MFCCs, is omitted, a DNN or another machine learning algorithm (cf. block 80) can be trained to transform a time series of vocal tract feature vectors directly into the acoustic speech output waveform (cf. block 78) (FIG. 6*c*). In a fully end-to-end model, the time series of frames of vocal tract data would not be pre-processed to feature vectors. Instead, the DNN or another machine learning algorithm (cf. block 80) can be trained to directly generate the acoustic waveform (cf. block 78) from the time series of vocal tract data frames (FIG. 6*d*).

Step 3: Using the voice prosthesis. The trained neural network can then be used to realize an electronic voice prosthesis, a medical device that can alternatively be referred to as a "voice graft", an "artificial voice", or a "voice transplant". A wide range of implementations are possible for the voice prosthesis. In practice, the choice will depend on the target patient scenario, i.e. the type of vocal impairment, the patient's residual vocal capabilities, the therapy goals, and aspects of the target setting, such as in-hospital vs. at home; bedridden vs. mobile.

Four elements can interact to provide a voice prosthesis: Vocal tract sensors, preferably light-weight, compact and unobtrusive; a computing device, ideally mobile and wirelessly connected; the machine learning algorithm; and an acoustic output device, ideally unobtrusive but in proximity to the patient. Next, implementation choices for each of these elements are discussed.

The first element are vocal tract sensors. A wide range of implementation options was discussed in the section "Step 1*b*: Creating the vocal tract training data", above. The choice and placement of sensors during algorithm training and use of the voice prosthesis are typically the same. The optimal choice of sensors depends on the patient scenario. Electromagnetic or ultrasonic sensing of the vocal tract are chosen based on the reliability with which elements of speech can be recognized for the target patient type and setting. An auxiliary lip and facial camera will be advantageous in many scenarios to increase the reliability of recognition. In scenarios where the patient has any residual vocal output, such as residual phonation or the ability to whisper, a microphone will be an advantageous sensor modality. If the extrinsic laryngeal muscles and neck musculature are active, surface EMG can be an advantageous auxiliary sensor. Sensors should be light-weight and compact so as to not impede the patients movement and articulation. In most mobile and at-home settings, unobtrusiveness will be an aspect of emotional and social importance to patients.

The second element of the voice prosthesis is a local computing device. It provides the computing power to carry out the trained machine learning algorithm or connects with a cloud-based computing platform where the algorithm is deployed, connects the algorithm with the acoustic output device, i.e. the loudspeaker, and provides a user interface. The requirements for portability and connectivity of the computing device depend on the patient scenario: For use at home, a mobile computing device is preferred. Compactness, affordability, and easy usability make a smartphone or tablet a preferred choice. It helps that a smartphone is not perceived as a prosthetic device, but as an item of daily use. In an ICU setting, by contrast, compactness and unobtrusiveness play a lesser role and the computing device can be integrated into a bedside unit. For home settings, a wireless connection, such as Bluetooth, between the sensor and the computing device will be desirable. In an ICU setting, on the other hand, wired connections are more acceptable. Thus, as a general rule, it is possible that a conversion of one or more is locally implemented on at least one mobile computing device of the patient, or is remotely implemented using cloud-computing.

The second element of the voice prosthesis is a local computing device. It provides the computing power to carry out the trained machine learning algorithm or connects with a cloud-based computing platform where the algorithm is deployed, connects the algorithm with the acoustic output device, i.e. the loudspeaker, and provides a user interface. The requirements for portability and connectivity of the computing device depend on the patient scenario: For use at home, a mobile computing device is preferred. Compactness, affordability, and easy usability make a smartphone or tablet a preferred choice. It helps that a smartphone is not perceived as a prosthetic device, but as an item of daily use. In an ICU setting, by contrast, compactness and unobtrusiveness play a lesser role and the computing device can be integrated into a bedside unit. For home settings, a wireless connection, such as Bluetooth®, between the sensor and the computing device will be desirable. In an ICU setting, on the other hand, wired connections are more acceptable. Thus, as a general rule, it is possible that a conversion of one or more is locally implemented on at least one mobile computing device of the patient, or is remotely implemented using cloud-computing.

The fourth element is an acoustic output device, for example a loudspeaker. Ideally, this loudspeaker is both unobtrusive and in proximity to the patient's mouth, to make for a natural appearance of the artificial voice output. The closest proximity can be achieved by integrating a loudspeaker in the sensor unit, located at the patient's throat, under the mandible, or on a headset cantilever in front of the patient's face. Alternatively, a simpler solution for smartphone based implementations would be to use the loudspeaker output of the smartphone.

Based on the range of the implementation options for each step above, a wide range of embodiments of the techniques described herein is possible. We describe four preferred embodiments of the invention for different patient scenarios. It is understood that combinations of various aspects of these embodiments can also be advantageous in these and other scenarios and that more embodiments of the invention can be generated from the implementation options discussed above. Also, the preferred embodiments described can apply to scenarios other than the ones mentioned in the description.

Preferred Embodiment 1: Radar and Video Based Method for Bedridden Patients

For a bedridden patient with no laryngeal airflow, such as a patient who is mechanically ventilated through a cuffed tracheostomy tube, embodiment 1 is a preferred embodiment. Such patients generally have no residual voice output and are not able to whisper. Therefore, the combination of radar sensing to obtain robust vocal tract signals and a video camera to capture lip and facial movements is preferred.

The main elements of the corresponding voice prosthesis are shown in FIG. 7. The patient (53) is confined to the patient bed (54), typically an ICU bed. A power supply (55), radar transmission and receiving electronics (56), signal processing electronics (57), a computing device (58), and audio amplifier (59) are contained in a bedside unit (60). A portable touchscreen device (61) such as a tablet serves as the user interface through which patient and care staff can interact with the system.

Two or more antennas (36) are used to collect reflected and transmitted radar signals that encode the time-varying vocal tract shape. The antennas are placed in proximity to the patient's vocal tract, e.g. under the right and left jaw bone. To keep their position stable relative to the vocal tract they can be attached directly to the patient's skin as patch antennas. Each antenna can send and receive modulated electromagnetic signals in a frequency band between 1 kHz and 12 GHz, optionally 1 GHz and 12 GHz, so that (complex) reflection and transmission can be measured. Possible modulations of the signal are: frequency sweep-, stepped frequency sweep-, pulse-, frequency comb-, frequency-, phase-, or amplitude modulation. In addition, a video camera (48) captures a video stream of the patient's face, containing information about the patient's lip and facial movements. The video camera is mounted in front of the patient's face on a cantilever (62) attached to the patient bed. The same cantilever can support the loudspeaker (63) for acoustic speech output.

The computing device (58) contained in the bedside unit (60) locally provides the necessary computing power to receive signals from the signal processing electronics (57) and the video camera (48), run the machine learning algorithm, output acoustic waveforms to the audio amplifier (59), and communicate wirelessly with the portable touchscreen device (61) serving as the user interface. The machine learning algorithm uses a deep neural network to transform the pre-processed radar signals and the stream of video images into an acoustic waveform in real time. The acoustic waveform is sent via the audio amplifier (59) to the loudspeaker (63).

The corresponding method for creating an artificial voice is as follows. An existing speech database is used to obtain audio training data for multiple target voices with different characteristics such as gender, age, and pitch. To create a corresponding body of vocal tract data, the sample text of the audio training data is read by a number of different speakers without speech impairment while their vocal tract signals are being recorded with the same radar sensor and video camera setup as for the eventual voice prosthesis. As the speakers read the sample text off a display screen, they follow the text along with an input stylus and timing cues are recorded. The timing cues are used to synchronize the vocal tract training data with the audio training data.

The audio training data sets of different target voices are separately combined with the synchronized vocal tract training data and used to train a deep neural network algorithm to convert radar and video data into the target voice. This results in a number of different DNNs, one for each target voice. The voice prosthesis is pre-equipped with these pre-trained DNNs.

To deal with the subject-to-subject variation in vocal tract signals, a pre-trained DNN is re-trained for a particular patient before use. To this end, first the pre-trained DNN that best matches the intended voice for the patient is selected. Then, the patient creates a patient-specific set vocal tract training data, by mouthing an excerpt of the sample text that was used to pre-train the DNNs, while vocal tract data are being recorded. This second vocal tract training data set is synchronized and combined with the corresponding audio sample of the selected target voice. This smaller, patient-specific second set of training data is now used to re-train the DNN. The resulting patient specific DNN is used in the voice prosthesis to transform the patient's vocal tract signal to voice output with the characteristics of the selected target voice.

Preferred Embodiment 2: Radar and Video Based Method for Mobile Patients

For a mobile patient with no laryngeal airflow, such as a patient whose larynx has been surgically removed, embodiment 2 is a preferred embodiment. Like the patient in embodiment 1, such patients also have no residual voice output and are not able to whisper. Therefore, the combination of radar sensing and a video camera to capture lip and facial movements is preferred in this case, too.

The main elements of the corresponding voice prosthesis are shown in FIG. 8. The patient (64) is mobile, so all elements of the voice prosthesis should be portable. A power supply (55), radar transmission and receiving electronics (56), signal processing electronics (57), and a wireless transmitter and receiver (65) are contained in a portable electronics unit (66). A portable touchscreen device (61) with a built-in loudspeaker (63) serves as the user interface for the patient.

As in embodiment 1, two or more antennas (36) are used to collect reflected and transmitted radar signals that encode the time-varying vocal tract shape. The antennas are placed in proximity to the patient's vocal tract, e.g. under the right and left jaw bone. To keep their position stable relative to the vocal tract they can be attached directly to the patient's skin. Each antenna can send and receive modulated electromagnetic signals in a frequency band between 1 kHz and 12 GHz, so that (complex) reflection and transmission can be measured. Possible preferred modulations of the signal are: frequency sweep-, stepped frequency sweep-, pulse-, frequency comb-, frequency-, phase-, or amplitude modulation.

In addition, a video camera (48) captures a video stream of the patient's face, containing information about the patient's lip and facial movements. For portability the video camera is mounted in front of the patient's face on a cantilever (62) worn by the patient like a microphone headset.

The portable touchscreen device (61) is also the computing device that locally provides the necessary computing power to receive the processed radar signals and the video images from the wireless transmitter (65), run the machine learning algorithm, output the acoustic speech waveforms via the built-in speaker (63), and provide the user interface on the touchscreen. The machine learning algorithm uses a deep neural network to transform the pre-processed radar signals and the stream of video images into an acoustic waveform in real time.

The corresponding method for creating an artificial voice is the same as in embodiment 1.

Preferred Embodiment 3: Low-Frequency Ultrasound and Video Based Method for Mobile Patients For a mobile patient with no laryngeal airflow, such as a patient whose larynx has been surgically removed, embodiment 3 is an alternative preferred embodiment. Instead of radar sensing, in this embodiment low-frequency ultrasound is used to characterize the time-varying shape of the vocal tract.

Figure 9:
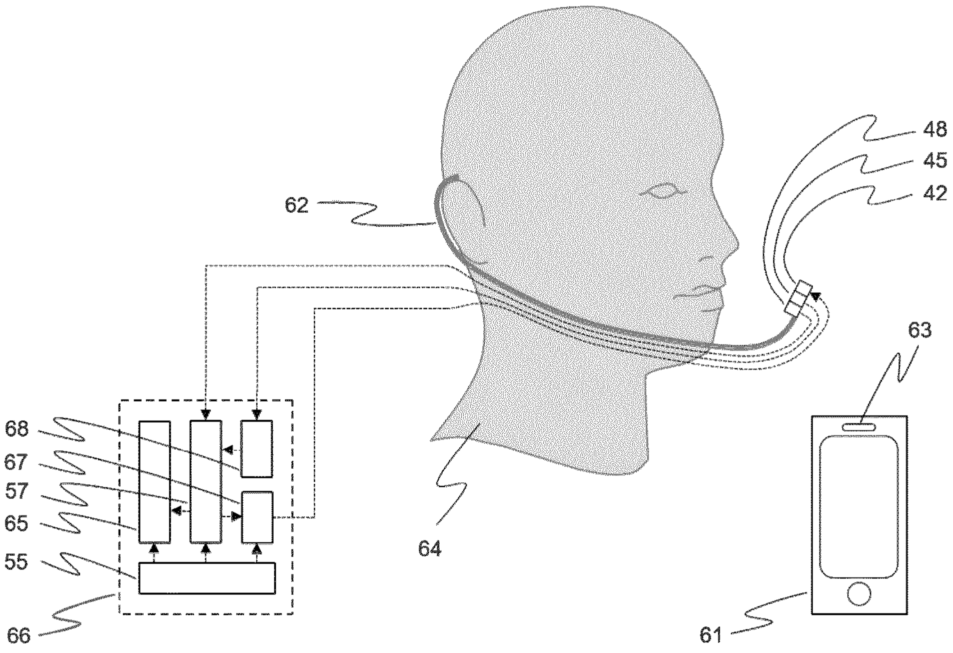
FIG. 9 schematically illustrates a voice prosthesis employing low-frequency ultrasound and video sensors for mobile patients according to various examples.

The main elements of the corresponding voice prosthesis are shown in FIG. 9. The patient (64) is mobile, so again all elements of the voice prosthesis should be portable. A power supply (55), an ultrasound waveform generator (67), an analog-to-digital converter (68), signal processing electronics (57), and a wireless transmitter and receiver (65) are contained in a portable electronics unit (66). A portable touchscreen device (61) with a built-in loudspeaker (63) serves as the user interface.

A low-frequency ultrasound loudspeaker (42) is used to emit ultrasound signals in the range of 20 to 30 kHz that are directed at the patient's mouth and nose. The ultrasound signals reflected from the patient's vocal tract are captured by an ultrasound microphone (45). The ultrasound loudspeaker and microphone are mounted in front of the patient's face on a cantilever (62) worn by the patient like a microphone headset.

With this setup, the complex reflection coefficient can be measured as a function of frequency. The frequency dependence of the reflection or transmission is measured by sending signals in a continuous frequency sweep, or in a series of wave packets with stepwide increasing frequencies, or by sending a short pulse and measuring the impulse response in a time-resolved manner.

In addition, a video camera (48) captures a video stream of the patient's face, containing information about the patient's lip and facial movements. The video camera is mounted on the same cantilever (62) as the ultrasound loudspeaker and microphone.

As in embodiment 2, the portable touchscreen device (61) is also the computing device. It locally provides the necessary computing power to receive the ultrasound signals converted by the analog-to-digital converter (68) and the video images via the wireless transmitter (65), run the machine learning algorithm, output the acoustic speech waveforms via the built-in speaker (63), and provide the user interface on the touchscreen. The machine learning algorithm uses a DNN to transform the pre-processed ultrasound signals and the stream of video images into an acoustic waveform in real time.

The corresponding method for creating an artificial voice is the same as in embodiments 1 and 2.

Preferred Embodiment 4: Audio and Video Based Method for Mobile Patients with Residual Voice For a mobile patient with residual voice output, such as residual phonation, a whisper voice, or a pure whisper without phonation, embodiment 4 is a preferred embodiment. For such a patient, the combination of an acoustic microphone to pick up the residual voice output and a video camera to capture lip and facial movements is preferred.

Figure 10:
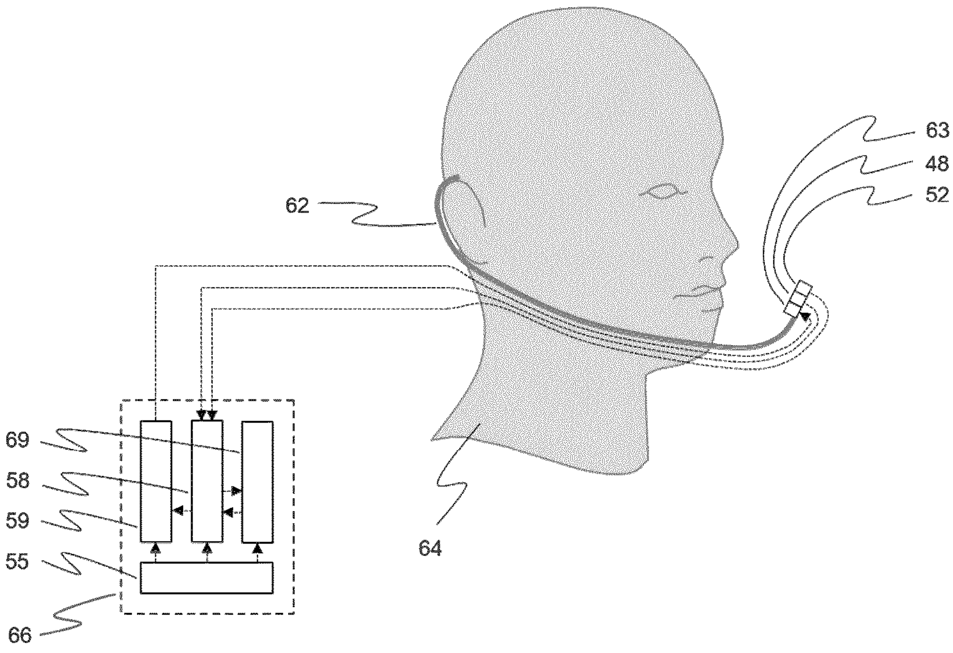
FIG. 10 schematically illustrates a voice prosthesis employing an audio and video sensor for mobile patients according to various examples.

The main elements of the corresponding voice prosthesis are shown in FIG. 10. As in embodiments 2 and 3, the patient is mobile, so all elements of the voice prosthesis should be portable. To minimize the number of separate components and maximize unobtrusiveness, no portable touchscreen device is used as a user interface and all electronics are contained in a portable electronics unit (66): a power supply (55), a computing device (58), an audio amplifier (59), and a user interface (69) such as a touch screen.

A microphone (52) capturing the acoustic signal of the residual voice and a video camera (48) capturing lip and facial movements are placed in front of the patient's face on a cantilever (62) worn by the patient like a microphone headset. The microphone and camera signals are sent to the computing device (59) which runs the machine learning algorithm and outputs the acoustic speech output via the audio amplifier (59) and a loudspeaker (63) that is also mounted on the cantilever in front of the patient's face. The machine learning algorithm uses a DNN to transform the acoustic and video vocal tract signals into an acoustic waveform in real time.

The corresponding method for creating an artificial voice differs from the previous embodiments. Since the residual voice depends strongly on the patient's condition and may even change over time, a patient specific DNN algorithm is trained for each patient.

An existing speech database is used to obtain audio training data for a target voice that matches the patient in characteristics such as gender, age, and pitch. To create a corresponding body of vocal tract data, the sample text of the audio training data is read by the patient with the same microphone and video camera setup as for the eventual voice prosthesis. As the patient reads the sample text off a display screen, he or she follows the text along with an input stylus and timing cues are recorded. The timing cues are used to synchronize the vocal tract training data with the audio training data.

The combined training data set is used to train the DNN algorithm to transform the patient's vocal tract signals, i.e. residual voice and lip and facial movements, into acoustic speech output. If over time the patient's residual voice output changes enough to degrade the quality of the speech output, the algorithm can be re-trained by recording a new set of vocal tract training data.

Summarizing, at least the following examples have been described above.

EXAMPLE 1. A method, comprising:

training a machine learning algorithm based on one or more reference audio signals of a speech output of a reference text, and one or more vocal tract signals associated with an articulation of the reference text by a patient.

EXAMPLE 2. The method of EXAMPLE 1, wherein multiple configurations of the machine learning algorithm are trained using at least one of multiple speech outputs having varying speech characteristics, or multiple articulations of the reference text having varying articulation characteristics, wherein the method further comprises:

selecting a configuration from the multiple configurations of the machine learning algorithm based on a patient dataset of the patient.

EXAMPLE 3. The method of EXAMPLE 1 or 2, further comprising:

synchronizing a timing of the one or more reference audio signals with a further timing of the one or more vocal tract signals.

EXAMPLE 4. The method of EXAMPLE 3, wherein said synchronizing comprises:

controlling a human-machine interface to provide temporal guidance to the patient when articulating the reference text in accordance with the timing of the one or more reference audio signals.

EXAMPLE 5. The method of EXAMPLE 3 or 4, wherein said synchronizing comprises:

controlling a human-machine-interface to obtain a temporal guidance from the patient when articulating the reference text.

EXAMPLE 6. The method of any one of EXAMPLEs 3 to 5, wherein said synchronizing comprises:

postprocessing at least one of the one or more reference audio signals and the one or more vocal-tract signals by changing a respective time.

EXAMPLE 7. The method of any one of EXAMPLEs 1 to 6, wherein the machine learning algorithm is trained end-to-end to convert a live articulation of the patient to a live speech output.

EXAMPLE 8. The method of any one of EXAMPLEs 1 to 6, wherein the machine learning algorithm is trained end-to-end to convert a live articulation of the patient to fragments of a live speech output.

EXAMPLE 9. The method of any one of the preceding EXAMPLEs, wherein the one or more reference audio signals and/or the one or more vocal-tract signals are provided by at least one of the patient or one or more other persons.

EXAMPLE 10. The method of any one of the preceding EXAMPLEs, further comprising:

receiving one or more live vocal tract signals of the patient, and based on the machine learning algorithm, converting the one or more live vocal-tract signals into associated one or more live audio signals comprising speech output.

EXAMPLE 11. The method of EXAMPLE 10, wherein said converting is locally implemented on at least one mobile computing device of the patient, or is remotely implemented using cloud-computing.

EXAMPLE 12. The method of EXAMPLE 10 or 11, further comprising:

recording at least a part of the one or more live vocal-tract signals using one or more sensors associated with at least one mobile computing device.

EXAMPLE 13. The method of EXAMPLE 12, wherein the one or more sensors are selected from the group comprising: a lip camera; a facial camera; a headset microphone; an ultrasound transceiver; a neck or larynx surface electromyogram; and a radar transceiver.

EXAMPLE 14. The method of any one of EXAMPLEs 10 to 13, further comprising:

outputting the one or more live audio signals using a speaker of at least one mobile computing device of the patient.

EXAMPLE 15. The method of any one of the preceding EXAMPLEs, wherein the patient is on mechanical ventilation through a tracheostomy, has undergone a partial or complete laryngectomy, or suffers from vocal fold paresis or paralysis.

EXAMPLE 16. The method of EXAMPLE 15, wherein the speech output of the reference text is provided by the patient prior to speech impairment.

EXAMPLE 17. A device comprising a control circuitry configured to:

receive one or more live vocal tract signals of a patient, based on a machine learning algorithm, convert the one or more live vocal tract signals into one or more associated live audio signals comprising a speech output, the machine learning algorithm being trained based on one or more reference audio signals of a speech output of a reference text, and one or more reference vocal tract signals of a patient associated with an articulation of the reference text by a patient.

EXAMPLE 18. The device of EXAMPLE 17, wherein the control circuitry is configured to execute the method of any one of the EXAMPLES 1 to 16.

Although the invention has been shown and described with respect to certain preferred embodiments, equivalents and modifications will occur to others skilled in the art upon the reading and understanding of the specification. The present invention includes all such equivalents and modifications and is limited only by the scope of the appended claims.

For instance, various examples have been described with respect to certain sensors used to record one or more vocal tract signals. Depending on the patient's condition, residual vocal capabilities, the therapy goals and the setting, different vocal tract sensors can be used. They can be unobtrusive and wearable: light weight and compactness; preferably low power consumption and wireless operation.

For further illustration, various examples have been described with respect to a trained machine learning algorithm. Depending on the computing power requirements in the transmission bandwidth, modifications are possible: for example, the trained machine learning algorithm could be deployed locally (i.e., on a mobile computing device) or remotely, i.e., using a cloud computing service. The mobile computing device can be used to connect one or more sensors with a platform executing the machine learning algorithm. The mobile computing device can also be used to output, via a loudspeaker, one or more audio signals including speech output determined based on the machine learning algorithm.

For further illustration, various examples have been described in which multiple configurations of the machine learning algorithm are trained using varying speech characteristics and/or varying articulation characteristics. In this regard, many levels of matching the speech characteristic to the patient characteristic are conceivable: gender, age, pitch, accent or dialect, etc. The matching can be done by selecting from a "library" of configurations of the machine learning algorithm, by modifying an existing configuration, or by custom recording the voice of a "voice donor".

For still further illustration, the particular type or sets of sensors is not germane to the functioning of the subject techniques. Different sensor types are advantageous in different situations: (i) lip/facial cameras. A camera recording the motion of the lips and facial features will be useful in most cases, since these cues are available in most disease scenarios, are fairly information-rich (cf. lip reading), and are easy to pick up with a light-weight, relatively unobtrusive setup. A modified microphone headset with one or more miniature CCD cameras mounted on the cantilever may be used. Multiple CCD cameras or depth-sensing cameras, such as cameras using time-of-flight technology may be advantageous to enable stereoscopic image analysis. (ii) Radar transceiver. Short-range radar operating in the frequency range between 1 and 12 GHz is an attractive technology for measuring the internal vocal tract configuration. These frequencies penetrate several centimeters to tens of centimeters into tissue and are safe for continuous use at the extremely low average power levels (microwatts) required. The radar signal can be emitted into a broad beam and detected either with a single antenna or in a spatially (i.e. angularly) resolved manner with multiple antennas. (iii) ultrasound transceiver. Ultrasound can be an alternative to radar sensing in measuring the vocal tract configuration. At frequencies in the range of 1-5 MHz, ultrasound also penetrates and images the pertinent tissues well and can be operated safely in a continuous way. Ultra-compact, chip based phased-array ultrasound transceivers are available for endoscopic applications. Ultrasound can also be envisioned to be used in a non-imaging mode. (iv) surface EMG sensors. Surface EMG sensors may provide complementary data to the vocal tract shape information, especially in cases where the extrinsic laryngeal musculature is present and active. In those cases, EMG may help by providing information on intended loudness (i.e. adding dynamic range to the speech output) and, more fundamentally, distinguishing speech from silence. The latter is a fundamental need in speech recognition, as the shape of the vocal tract alone does not reveal whether or not acoustic excitation (phonation) is present. (v) acoustic microphone. Acoustic microphones make sense as (additional) sensors in all cases with residual voice present. Note that in this context, "residual voice" may include a whispering voice. Whispering needs air flow through the vocal tract, but does not involve phonation (i.e. vocal fold motion). In many cases, picking up a whispered voice, perhaps in combination with observing lip motion, may be enough to reconstruct and synthesize natural sounding speech. In many scenarios, this would greatly simplify speech therapy, as it reduces the challenge from getting the patient to speak to teaching the patient to whisper. Microphones could attach to the patient's throat, under the mandible, or in front of the mouth (e.g. on the same headset cantilever as a lip/facial camera).

For still further illustration, various examples have been described in connection with using a machine learning algorithm to transform vocal-tract signals into audio signals associated with speech. It is not mandatory to use a machine learning algorithm; other types of algorithms may be used for the transformation.

LIST OF REFERENCE NUMERALS

Figure 1:
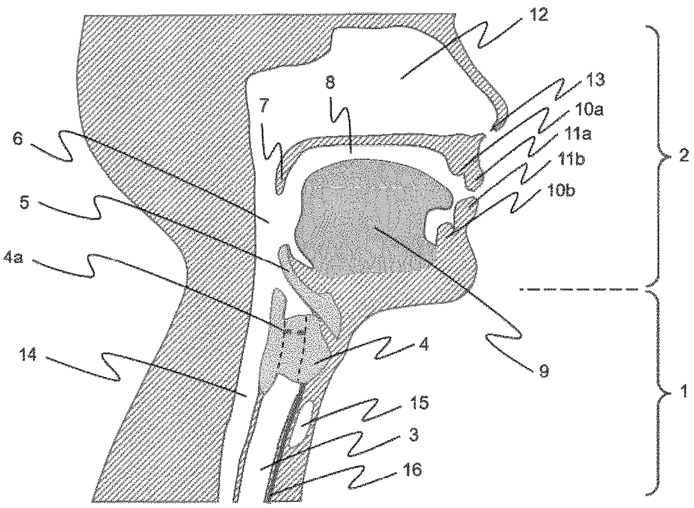
FIG. 1 schematically illustrates the anatomy relevant to physiologic voice production and its impairments.
Figure 2:
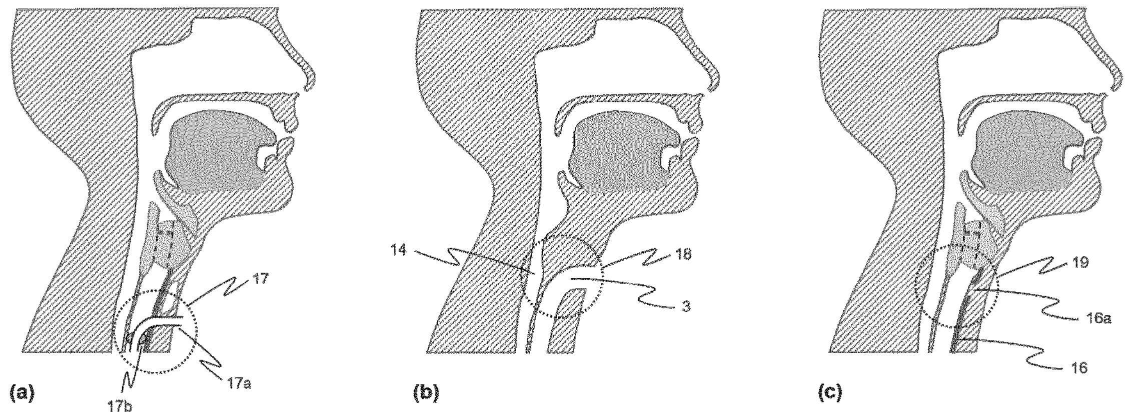
FIG. 2 schematically illustrates different causes of aphonia: (a) tracheostomy, (b) laryngectomy, (c) recurrent nerve injury.
Figure 3:
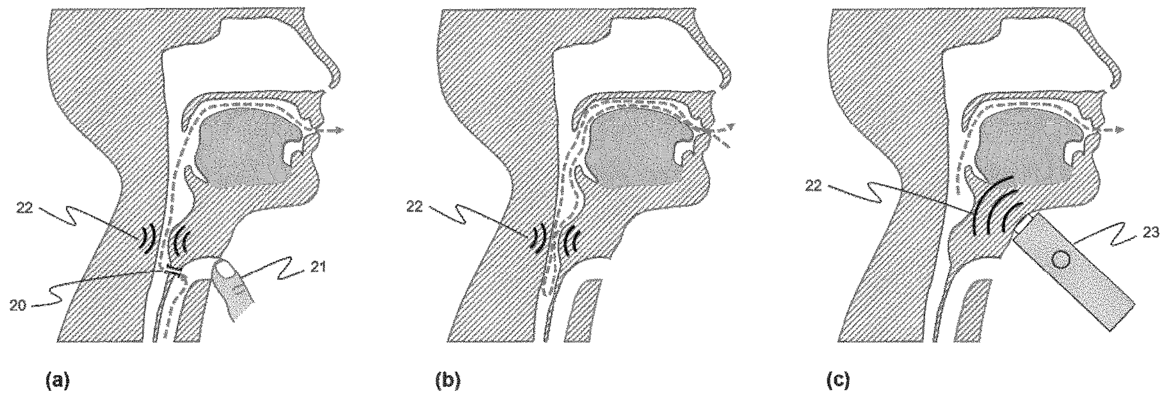
FIG. 3 schematically illustrates different voice rehabilitation options: (a) TEP, (b) esophageal speech, (c) electrolarynx.

FIG. 1: Schematic of the Anatomy Relevant to Physiologic Voice Production and its Impairments
- 1 anatomical structures involved in phonation: lungs (not shown), trachea, and larynx ("source")
- 2 anatomical structures involved in articulation: vocal tract ("filter")
- 3 trachea
- 4 larynx
- 4*a* glottis
- 5 epiglottis
- 6 pharynx
- 7 velum
- 8 oral cavity
- 9 tongue
- 10*a* upper teeth
- 10*b* lower teeth
- 11*a* upper lip
- 11*b* lower lip
- 12 nasal cavity
- 13 nostrils
- 14 esophagus
- 15 thyroid
- 16 recurrent laryngeal nerve FIG. 2: Schematic of Different Causes of Aphonia (a) Tracheostomy
- 17 tracheostomy for mechanical ventilation
- 17*a* tracheostomy tube
- 17*b* inflated cuff (b) Laryngectomy
- 18 tracheostoma after laryngectomy
- 3 trachea
- 14 esophagus (c) Recurrent Nerve Injury
- 19 laryngeal nerve injury after thyroidectomy
- 16 recurrent laryngeal nerve
- 16*a* nerve injury FIG. 3: Schematic of Different Voice Rehabilitation Options (a) Tracheoesphageal Puncture (TEP)
- 20 tracheoesophageal puncture and valve
- 21 finger
- 22 vibrations (b) Esophageal Speech
- 22 vibrations (c) Electrolarynx
- 23 electrolarynx
- 22 vibrations FIG. 4: Schematic of an Example Implementation (a) Step 1*a*: Creating the Audio Training Data
- 24 sample text
- 25 healthy speaker
- 26 microphone
- 27 audio training data (b) Step 1*b*: Creating the Vocal Tract Training Data
- 28 display with sample text
- 29 impaired patient
- 30 vocal tract sensors
- 31 vocal tract training data (c) Step 1*c*: Synchronizing Audio and Vocal Tract Training Data
- 27 audio training data
- 31 vocal tract training data (d) Step 2: Training the Algorithm
- 27 audio training data
- 31 vocal tract training data
- 32 trained machine learning algorithm (e) Step 3: Using the Voice Prosthesis
- 29 impaired patient
- 30 vocal tract sensors
- 32 trained machine learning algorithm
- 33 wireless connection
- 34 mobile computing device
- 35 acoustic speech output FIG. 5: Schematic of Different Implementation Options for Vocal Tract Sensors (a) Microwave Radar Sensing
- 36 radar antenna
- 37 emitted radar signal
- 38 backscattered/transmitted radar signal (b) Ultrasound Sensing
- 39 ultrasound transducer
- 40 emitted ultrasound signal
- 41 backscattered ultrasound signal (c) Low-Frequency Ultrasound
- 42 ultrasound loudspeaker
- 43 emitted ultrasound signal
- 44 reflected ultrasound signal
- 45 ultrasound microphone (d) Lip and Facial Camera
- 46 ambient light
- 47 reflected light
- 48 video camera (e) Surface Electromyography
- 49 surface electromyography sensors (for extralaryngeal musculature)
- 50 surface electromyography sensors (for neck and facial musculature (f) Acoustic Microphone
- 51 residual acoustic voice signal
- 52 acoustic microphone FIG. 6: Schematic of Different Implementation Options for Processing Vocal Tract Signals (a) Using Elements of Speech and MFCCs as Intermediate Representations of Speech

70 vocal tract data: series of frames
71 data pre-processing
72 time series of feature vectors
73 speech recognition algorithm
74 elements of speech: phonemes, syllables, words
75 speech synthesis algorithm
76 mel-frequency cepstral coefficients
77 acoustic waveform synthesis
78 acoustic speech waveform (b) Using MFCCs as Intermediate Representations of Speech

70 vocal tract data: series of frames
71 data pre-processing
72 time series of feature vectors
76 mel-frequency cepstral coefficients
77 acoustic waveform synthesis
78 acoustic speech waveform
79 deep neural network algorithm (c) End-to-End Machine Learning Algorithm Using No Intermediate Representations of Speech

70 vocal tract data: series of frames
71 data pre-processing
72 time series of feature vectors
78 acoustic speech waveform
80 end-to-end deep neural network algorithm (d) End-to-End Machine Learning Algorithm Using No Explicit Pre-Processing and No Intermediate Representations of Speech

70 vocal tract data: series of frames
78 acoustic speech waveform
80 end-to-end deep neural network algorithm FIG. 7: Schematic of Voice Prosthesis for Preferred Embodiment 1: Radar and Video Based Method for Bedridden Patients

36 radar antennas
48 video camera
53 bedridden patient
54 patient bed
55 power supply
56 radar transmission and receiving electronics
57 signal processing electronics
58 computing device
59 audio amplifier
60 bedside unit
61 mobile computing device with touchscreen
62 cantilever
63 loudspeaker FIG. 8: Schematic of Voice Prosthesis for Preferred Embodiment 2: Radar and Video Based Method for Mobile Patients

36 radar antennas
48 video camera
55 power supply
56 radar transmission and receiving electronics
57 signal processing electronics
61 mobile computing device with touchscreen
62 cantilever
63 loudspeaker
64 mobile patient
65 wireless transmitter and receiver
66 portable electronics unit FIG. 9: Schematic of Voice Prosthesis for Preferred Embodiment 3: Low-Frequency Ultrasound and Video Based Method for Mobile Patients

42 ultrasound loudspeaker
45 ultrasound microphone
48 video camera
55 power supply
57 signal processing electronics
61 mobile computing device with touchscreen
62 cantilever
63 loudspeaker
64 mobile patient
65 wireless transmitter and receiver
66 portable electronics unit
67 ultrasound waveform generator
68 analog-to-digital converter FIG. 10: Schematic of Voice Prosthesis for Preferred Embodiment 4: Audio and Video Based Method for Mobile Patients with Residual Voice

48 video camera
52 microphone
55 power supply
58 computing device
59 audio amplifier
62 cantilever
63 loudspeaker
64 mobile patient
66 portable electronics unit
69 user interface

The invention claimed is:

1. A method for use in an electronic voice prosthesis for creating an artificial voice for a patient with missing phonation but at least residual articulation function, the method comprising:

transmitting a radio-frequency signal, using a transmit antenna attached to skin of the patient at a first location of the head of the patient near the vocal tract of the patient, when the patient articulates silent speech;

receiving the radio-frequency signal that is influenced by internal components of the vocal tract of the patient using a receive antenna attached to the skin of the patient at a second location of the head of the patient near the vocal tract of the patient, the received radio-frequency signal encoding information representative of a time-varying shape of the internal components of the vocal tract when the patient articulates the silent speech;

selecting a trained end-to-end deep neural network algorithm from multiple predefined end-to-end deep neural network algorithms associated with multiple target voices; and using the selected trained end-to-end deep neural network algorithm to convert the received radio-frequency signal directly to an acoustic speech output for the silent speech.

2. The method according to claim 1, wherein the patient is on mechanical ventilation, has undergone a partial or complete laryngectomy, or suffers from vocal fold paresis or paralysis.

3. The method according to claim 1, wherein the using the selected trained end-to-end deep neural network algorithm to convert the received radio-frequency signal to the acoustic speech output comprises converting the received radio-frequency signal to the acoustic speech output using a convolutional neural network, wherein the convolutional neural network is trained to directly convert the received radio-frequency signal to the acoustic speech output.

4. The method according to claim 1, wherein the using the selected trained end-to-end deep neural network algorithm to convert the received radio-frequency signal to the acoustic speech output comprises converting the received radio-frequency signal to the acoustic speech output using a convolutional neural network, wherein the convolutional neural network is trained to convert the received radio-frequency signal to elements of speech, such as phonemes, syllables or words, which are then synthesized to the acoustic speech output.

5. The method according to claim 1, wherein the using the selected trained end-to-end deep neural network algorithm to convert the received radio-frequency signal to the acoustic speech output comprises converting the received radio-frequency signal to the acoustic speech output using a convolutional neural network, wherein the convolutional neural network is pre-trained based on one or more healthy speakers and further impaired patients and re-trained for the patient.

6. The method according to claim 1, further comprising recording the radio-frequency signal using a radar transceiver.

7. The method according to claim 6, wherein the transmitting the radio-frequency signal comprises transmitting electromagnetic waves in a frequency range of 1 kHz to 12 GHZ, optionally microwaves between 1 GHz and 10 GHz.

8. The method according to claim 1, wherein the electronic voice prosthesis comprises a mobile computing device, and wherein the mobile computing device is a smart phone or a tablet carrying out the conversion of the received radio-frequency signal to the acoustic speech output locally on the device.

9. The method according to claim 1, wherein the electronic voice prosthesis comprises a mobile computing device, and wherein the mobile computing device is a smart phone or a tablet connected to the internet and the conversion of the received radio-frequency signal to the acoustic speech output is carried out on a remote computing platform.

10. The method according to claim 1, further comprising re-training the selected trained end-to-end deep neural network algorithm for the patient and subsequently using the re-trained selected trained end-to-end deep neural network algorithm for conversion of the received radio-frequency signal directly to the acoustic speech output for the silent speech.

11. The method according to claim 1, wherein no acoustic speech parameters, such as mel-frequency cepstral coefficients, are output by the selected trained end-to-end deep neural network algorithm as intermediate representations of speech.

12. A device for a patient with missing or impaired phonation but at least residual articulation function, wherein the device comprises:

at least one transmitting antenna configured to transmit one or more radio-frequency signals, wherein the one or more radio-frequency signals comprise one or more radiation patterns configured to overlap with a vocal tract of the patient; and at least one receiving antenna configured to collect radio-frequency signal data associated with a time-varying shape of internal components of the vocal tract of the patient when the patient articulates silent speech, wherein the at least one transmitting antenna and the at least one receiving antenna are configured to be coupled to skin of the patient at one or more locations on the head of the patient near the vocal tract of the patient, wherein the device is configured to select a trained end-to-end deep neural network algorithm from multiple predefined end-to-end deep neural network algorithms associated with multiple target voices, wherein the device is configured to directly convert the collected radio-frequency signal data to an acoustic speech output using the selected trained end-to-end deep neural network algorithm.

* * * * *